United States Patent
Sundermann et al.

(10) Patent No.: US 7,271,192 B2
(45) Date of Patent: Sep. 18, 2007

(54) SUBSTITUTED 2-PYRROLIDINE-2-YL-1H-INDOLE COMPOUNDS

(75) Inventors: Corinna Sundermann, Aachen (DE); Bernd Sundermann, Aachen (DE); Helmut Buschmann, Esplugues de Llobregat (ES); Hagen-Heinrich Hennies, Simmerath (DE)

(73) Assignee: Gruenenthal GmbH, Aachen (DE)

( * ) Notice: Subject to any disclaimer, the term of this patent is extended or adjusted under 35 U.S.C. 154(b) by 124 days.

(21) Appl. No.: 10/861,426

(22) Filed: Jun. 7, 2004

(65) Prior Publication Data

US 2005/0014815 A1 Jan. 20, 2005

Related U.S. Application Data

(63) Continuation of application No. PCT/EP02/13613, filed on Dec. 2, 2002.

(30) Foreign Application Priority Data

Dec. 6, 2001 (DE) ................. 101 59 922

(51) Int. Cl.
*A61K 31/404* (2006.01)
*C07D 209/04* (2006.01)

(52) U.S. Cl. ............ 514/415; 548/465; 548/466; 546/112; 546/139; 546/146; 514/412

(58) Field of Classification Search ............ 548/465, 548/466; 514/412, 415; 546/112, 139, 146
See application file for complete search history.

(56) References Cited

U.S. PATENT DOCUMENTS 6,245,761 B1   6/2001   Britton et al.

FOREIGN PATENT DOCUMENTS

| WO | WO-9311106 A1 | 6/1993 |
| WO | WO-9314087 A1 | 7/1993 |
| WO | WO-9506636 A1 | 3/1995 |
| WO | WO-0228839 A1 | 4/2002 |

OTHER PUBLICATIONS

Street et al (1987): STN International HCAPLUS database, Columbus (Ohio), accession No. 1988: 55922.*

A. Fuerstner et al. "Site Selective Formation of Low-Valent Titanium Reagents: an Instant Procedure for the Reductive Coupling of Oxo Amides to Indoles" *J. Org. Chem.* (1994) 59:5215-5229.
G. Foster et al. "The Reactions of Some Heterocyclic Quaternary Salts wit Potassium Cyanide" *Chemical Comm.* (1968) Bd. 22, S. 1440-1441.
A. Fuerstner et al. "Carbonyl Coupling Reactions Catalytic In Titanium and the Use of Commercial Titanium Powder for Organic Synthesis" *J. Am. Chem. Soc.* (1995) 117:4468-4475.
P. Chabrier et al. "Nitric oxide synthases: targets for therapeutic strategies in neurological diseases" *Cell. Mol. Life Sci.* (1999) 55:1029-1035.
A. Fuerstner et al. "Ethyl 5-chloro-3-phenylindole-2-carboxylate" *Org. Synth.* (1999) 76:142-150.
L. Lassen et al. "Nitric oxide synthase inhibition in migraine" *The Lancet* (1997) 349:401-402.
L. Thomsen et al. "Nitric Oxide Theory of Migraine" *Clinical Neuroscience* (1998) 5:28-33.
I. Green et al. "Nitric oxide: from basic research to clinical applications" *DDT* (1999) 4(2):47-49.
A. Hobbs et al. "Inhibition of Nitric Oxide Synthase as a Potential Therapeutic Target" *Annu. Rev. Pharmacol. Toxicol.* (1999) 39:191-220.
L. Ignarro "Stickstoffmonoxid: ein einzigartiges endogens Signalmolekuel in der Gafaeßbiologie (Novel-Vortrag)" *Angew. Chem.* (1999) 111:2002-2013.
F. Murad "Die Entdeckung einiger biologischer Wirkungen von Stickstoffmonoxid und seiner Rolle fuer die Zellkommunikation (Nobel-Vortrag)" *Angrew. Chem.* (1999) 111:1976-1989.

* cited by examiner

*Primary Examiner*—Golam M. M. Shameem
(74) *Attorney, Agent, or Firm*—Crowell & Moring LLP

(57) ABSTRACT

Novel 2-pyrrolidin-2-yl-1H-indole compounds corresponding to formula (I)

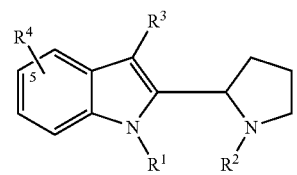

wherein $R^1$, $R^2$, $R^3$ and $R^4$ have the meanings given in the description, and pharmaceutical compositions containing these compounds, as well as processes for the preparation of such compounds and intermediate products of this process, and related methods of treatment.

19 Claims, No Drawings

SUBSTITUTED 2-PYRROLIDINE-2-YL-1H-INDOLE COMPOUNDS

CROSS-REFERENCE TO RELATED APPLICATIONS

This application is a continuation of International Patent Application No. PCT/EP02/13613, filed Dec. 2, 2002, designating the United States of America, and published in German as WO 03/048156 A1, the entire disclosure of which is incorporated herein by reference. Priority is claimed based on Federal Republic of Germany Patent Application No. DE 101 59 922.6, filed Dec. 6, 2001.

FIELD OF THE INVENTION

The invention relates to substituted 2-pyrrolidin-2-yl-1H-indole compounds, processes for their preparation, pharmaceutical formulations which comprise these compounds and the use of the 2-pyrrolidin-2-yl-1H-indole compounds according to the invention for the preparation of a pharmaceutical formulation for inhibition of NO synthase and for methods of treatment of, inter alia, migraine.

BACKGROUND OF THE INVENTION

Nitrogen monoxide (NO) regulates numerous physiological processes, inter alia neurotransmission, relaxation and proliferation of the smooth musculature, adhesion and aggregation of thrombocytes and tissue injury and inflammation. Because of the large number of signal functions, NO is associated with a number of diseases (see e.g. L. J. Ignarro, Angew. Chem. (1999), 111, 2002-2013 and F. Murad, Angew. Chem. Int. Ed. (1999), 111, 1976-(1999), 111, 2002-2013 and F. Murad, Angew. Chem. Int. Ed. (1999), 111, 1976-1989). The enzyme responsible for the physiological formation of NO, NO synthase (NOS), plays an important role here in the therapeutic influencing of these diseases. Three different iso-forms of NO synthase, namely the two constitutive forms nNOS and eNOS and the inducible form iNOS, have so far been identified (A. J. Hobbs, A. Higgs, S. Moncada, Annu. Rev. Pharmacol. Toxicol. (1999), 39, 191-220; I. C. Green, P.-E. Chabrier, DDT (1999), 4, 47-49; P.-E. Chabrier et al., Cell. Mol. Life Sci. (1999), 55, 1029-1035).

Inhibition of NO synthase opens up new therapy set-ups for various diseases connected with NO (A. J. Hobbs et al., Annu. Rev. Pharmacol. Toxicol. (1999), 39, 191-220; I. C. Green, P.-E. Chabrier, DDT (1999), 4, 47-49; P.-E. Chabrier et al., Cell. Mol. Life Sci. (1999), 55, 1029-1035), such as, for example, migraine (L. L. Thomsen, J. Olesen, Clinical Neuroscience (1998), 5, 28-33; L. H. Lassen et al., The Lancet (1997), 349, 401-402), septic shock, neurodegenerative diseases, such as multiple sclerosis, Parkinson's disease, Alzheimer's disease or Huntington's disease, inflammations, inflammation pain, cerebral ischaemia, diabetes, meningitis and arteriosclerosis. Furthermore, inhibition of NOS can have an effect on wound healing, on tumors and on angiogenesis, as well as effecting a non-specific immunity against microorganisms (A. J. Hobbs et al., Annu. Rev. Pharmacol. Toxicol. (1999), 39, 191-220).

Active compounds which inhibit NO synthase and are known to date are, in addition to L-NMMA and L-NAME—i.e. analogs of L-arginine, from which NO and citrulline are formed in vivo with involvement of NOS—inter alia S-methyl-L-citrulline, aminoguanidine, S-methylisourea, 7-nitroindazole and 2-mercaptoethylguanidine (A. J. Hobbs et al., Annu. Rev. Pharmacol. Toxicol. (1999), 39, 191-220).

SUMMARY OF THE INVENTION

One object of the present invention is to provide new active NOS inhibitors.

Surprisingly, it has been found that substituted 2-pyrrolidin-2-yl-1H-indole compounds corresponding to formula (I)

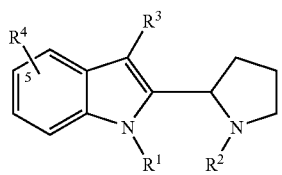

wherein $R^1$ denotes H, alkyl, cycloalkyl, alkyl-cycloalkyl, alkyl-aryl or alkyl-heterocyclyl;

$R^2$ denotes H, alkyl, cycloalkyl, alkyl-cycloalkyl, alkyl-aryl, alkyl-heterocyclyl, C(=O)—$R^{20}$ or SO$_2$—$R^{21}$;

$R^3$ denotes alkyl, aryl or heterocyclyl;

$R^4$ denotes H, F, Cl, Br, I, —CN, OR$^{40}$, alkyl, cycloalkyl or NO$_2$;

$R^{20}$ denotes alkyl, cycloalkyl, alkyl-cycloalkyl, aryl, alkyl-aryl, heterocyclyl, alkyl-heterocyclyl, OR$^{200}$ or NHR$^{201}$;

$R^{21}$ denotes alkyl, aryl, alkyl-aryl, heterocyclyl or alkyl-heterocyclyl;

$R^{40}$ denotes H, alkyl, cycloalkyl, alkyl-cycloalkyl, aryl or alkyl-aryl;

$R^{200}$ denotes alkyl, cycloalkyl, alkyl-cycloalkyl, aryl, alkyl-aryl, heterocyclyl or alkyl-heterocyclyl; and $R^{201}$ denotes alkyl, aryl, alkyl-aryl, heterocyclyl or alkyl-heterocyclyl;

wherein the compounds of the formula (I) are in the form of their racemates, their pure stereoisomers, in particular enantiomers or diastereomers, or in the form of mixtures of the stereoisomers, in particular of the enantiomers or diastereomers, in any desired mixture ratio; in the form shown or in the form of their acids or their bases or in the form of their salts, in particular the physiologically acceptable salts, or in the form of their solvates, in particular the hydrates;

are very active NOS inhibitors.

These compounds are new with the exception of 2-(3-phenyl-1H-indol-2-yl)-1-(trifluoroacetyl)-pyrrolidine (A. Fürstner et al., J. Org. Chem. (1994), 59, 5215-5229); α-methyl-2-(1-methyl-2-pyrrolidinyl)-indole-3-acetic acid methyl ester, 3-(1-cyanoethyl)-2-(1-methyl-2-pyrrolidinyl)-indole and 2-(1-methyl-2-pyrrolidinyl)-3-vinylindole (G. H. Foster, J. Harley-Mason, Chem. Commun. (1968), 1440-1441); which have been described as such in the prior art without an NOS-inhibiting (or any other pharmacological or therapeutic) action of these substances having been disclosed. This invention therefore also provides these compounds mentioned last as regards their use in a medicament and in particular for the preparation of a medicament for inhibition of NO synthase and for treatment of migraine, septic shock, multiple sclerosis, Parkinson's disease, Alzheimer's disease, Huntington's disease, inflammations, inflammation pain, cerebral ischaemia, diabetes, meningitis, arteriosclerosis and/or for wound healing.

In the context of this invention, the terms "alkyl", "$C_{1-6}$-alkyl", "$C_{1-4}$-alkyl" and "$C_{1-3}$-alkyl" include acyclic saturated or unsaturated hydrocarbon radicals, which can be branched or straight-chain and unsubstituted or monosubstituted or polysubstituted by identical or different substituents, having (as in the case of $C_{1-6}$-alkyl) 1 to 6 (i.e. 1, 2, 3, 4, 5 or 6), having (as in the case of $C_{1-4}$-alkyl) 1 to 4 (i.e. 1, 2, 3 or 4) or having (as in the case of $C_{1-3}$-alkyl) 1 to 3 (i.e. 1, 2 or 3) C atoms. The term "alkyl" in this context includes "alkanyls", "alkenyls" and "alkynyls". "Alkenyls" have at least one C—C double bond (but no C—C triple bond) and "alkynyls" have at least one C—C triple bond, while "alkanyls" have no C—C multiple bonds. "$C_{1-4}$-alkanyls" are alkanyls having 1, 2, 3 or 4 carbon atoms, "$C_{1-8}$-alkanyls" are alkanyls having 1, 2, 3, 4, 5, 6, 7 or 8 carbon atoms, while "$C_{2-8}$-s-alkenyls" are alkenyls having 2, 3, 4, 5, 6, 7 or 8 C atoms. Alkyl is preferably chosen from the group which includes methyl, ethyl, n-propyl, 2-propyl, n-butyl, iso-butyl, sec-butyl, tert-butyl, n-pentyl, iso-pentyl, neo-pentyl, n-hexyl, 2-hexyl, n-heptyl, n-octyl, n-nonyl, n-decyl, n-dodecyl; ethenyl (vinyl), ethynyl, propenyl (—CH$_2$CH═CH$_2$, —CH═CH—CH$_3$, —C(═CH$_2$)—CH$_3$), propynyl (—CH$_2$—C≡CH, —C≡C—CH$_3$), butenyl, butynyl, pentenyl, pentynyl, hexenyl, hexynyl, octenyl and octynyl.

In the context of this invention, "cycloalkyl" denotes an alicyclic saturated or unsaturated hydrocarbon radical, wherein the radical can be unsubstituted or monosubstituted or polysubstituted by identical or different substituents and optionally benzo-fused; the expression "cycloalkyl" furthermore also includes bi-, tri- or polycyclic alicyclic radicals, e.g. adamantyl. "$C_{3-8}$-Cycloalkyl" represents a cycloalkyl having 3, 4, 5, 6, 7 or 8 C atoms in the ring. By way of example, cycloalkyl represents cyclopropyl, cyclobutyl, cyclopentyl, cyclohexyl, cycloheptyl, cyclooctyl, cyclopentenyl, cyclohexenyl, cycloheptenyl, cyclooctenyl or adamantyl.

For the purposes of the present invention, the expression "aryl" is to be understood as meaning a radical which is chosen from the group which includes phenyl, naphthyl, anthracenyl and biphenyl, and is unsubstituted or monosubstituted or polysubstituted by identical or different substituents. The aryl radicals can also be fused with further saturated, (partly) unsaturated or aromatic ring systems. Each aryl radical can be unsubstituted or mono- or polysubstituted, wherein the substituents on the aryl can be identical or different and can be in any desired position of the aryl.

The expression "heterocyclyl" represents a monocyclic or polycyclic organic radical in which at least one ring contains 1 heteroatom or 2, 3, 4 or 5 identical or different heteroatoms which is/are chosen from the group which contains N, O and S, wherein the radical is saturated or unsaturated and is unsubstituted or monosubstituted or polysubstituted by identical or different substituents. In the context of this invention, examples of heterocyclyl radicals are monocyclic five-, six- or seven-membered organic radicals having 1 heteroatom or 2, 3, 4 or 5 identical or different heteroatoms, which is/are nitrogen, oxygen and/or sulfur, and benzo-fused analogs thereof. The "heteroaryl" radicals are those heterocyclyls in which the ring, of which there is at least one, which contains the heteroatom(s) forms a heteroaromatic sub-group of the heterocyclyl radicals. Each heteroaryl radical can be unsubstituted or monosubstituted or polysubstituted by identical or different substituents. In the context of the present invention, examples of heterocyclyl radicals are pyrrolidinyl, tetrahydrofuryl, piperidinyl, piperazinyl, morpholinyl, imidazolidinyl and benzopiperidinyl. Examples of heterocyclyls which at the same time are heteroaryl radicals are pyrrolyl, pyrazolyl, imidazolyl, pyridazinyl, pyrimidinyl, pyrazinyl and, in particular, furanyl, thienyl, isoxazolyl and pyridinyl, as well as benzo-fused analogs thereof. All these radicals can in each case be unsubstituted or monosubstituted or polysubstituted by identical or different substituents.

For the purposes of the present invention, the expressions "alkyl-cycloalkyl", "($C_{1-3}$-alkyl)-$C_{3-8}$-cycloalkyl", "alkyl-heterocyclyl", "alkyl-aryl", "$C_{1-4}$-alkanyl-aryl" and "$C_{1-4}$-alkenyl-aryl" mean that the cycloalkyl, heterocyclyl or aryl radical is bonded to the compound substituted with it via an alkyl group or alkanyl or alkenyl group.

In connection with "alkyl", "alkanyl", "alkenyl", "alkynyl" and "cycloalkyl", in the context of this invention the term "substituted" is understood as meaning substitution of a hydrogen atom by, for example, F, Cl, Br, I, —CN, NH$_2$, NH-alkyl, NH-alkyl-aryl, N(alkyl)$_2$, NO, NO$_2$, SH, S-alkyl, S—CF$_3$, OH, O-alkyl, O—CF$_3$, O-aryl, O-alkyl-aryl, O-alkyl-OH, O-alkyl-O-alkyl, O-alkyl-O-alkyl-OH, CO$_2$H, CO$_2$-alkyl, CO$_2$-alkyl-aryl, SO-alkyl, SO$_2$-alkyl, cycloalkyl, aryl or heterocyclyl, wherein polysubstituted radicals are to be understood as meaning those radicals which are polysubstituted, e.g. di- or trisubstituted, either on different or on the same atoms, for example trisubstituted at the same C atom, as in the case of CF$_3$ or —CH$_2$CF$_3$, or at different sites, as in the case of —CH(OH)—CH═CCl—CH$_2$Cl. Polysubstitution can be by identical or different substituents.

In the context of this invention, in respect of "aryl", "heterocyclyl" and "heteroaryl" "monosubstituted" or "polysubstituted" is understood as meaning monosubstitution or polysubstitution, e.g. di-, tri- or tetrasubstitution, or one or more hydrogen atoms of the ring system by a suitable substituent. Where the meaning of these suitable substituents in connection with "aryl", "heterocyclyl" or "heteroaryl" is not defined elsewhere in the description or in the claims, suitable substituents are F, Cl, Br, I. —CN, NH$_2$, NH-alkyl, NH-aryl, NH-alkyl-aryl, N(alkyl)$_2$, NO, NO$_2$, SH, S-alkyl, S—CF$_3$, OH, O-alkyl, O—CF$_3$, O-cycloalkyl, O-aryl, O-alkyl-cycloalkyl, O-alkyl-aryl, CHO, C(═O)C$_{1-6}$-alkyl, C(═O)CF$_3$, C(═O)aryl, C(═O)—C$_{1-6}$-alkyl-aryl, CO$_2$H, CO$_2$alkyl, S(O)-alkyl, SO$_2$-alkyl, CF$_3$, alkyl, cycloalkyl, aryl and/or heterocyclyl; on one or optionally different atoms (wherein a substituent can be optionally substituted in its turn). Polysubstitution in this context is by identical or different substituents.

For the purposes of the present invention, "benzo-fused" means that a benzene ring is fused on to another ring.

In the context of this invention, pharmaceutically acceptable salts and physiologically acceptable salts are those salts of the compounds of the general formula (I) according to the invention which are physiologically acceptable when used pharmaceutically—in particular when used on mammals and/or humans. Such pharmaceutically acceptable salts can be formed, for example, with inorganic or organic acids, or, in the case where the compounds according to the invention are acids, in particular carboxylic acids, with bases.

The pharmaceutically acceptable salts of the compounds of the general formula (I) according to the invention are preferably formed with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid. If the compounds according to the invention are acids, in particular carboxylic acids, the pharmaceutically acceptable salts can also be formed by reaction with bases, such as e.g. sodium hydroxide, sodium bicarbonate or sodium carbonate. The salts formed are, inter alia, hydrochlorides, hydrobromides, phosphates, carbonates, bicarbonates, formates, acetates, oxalates, succinates, tartrates, fumarates, citrates and glutamates, and sodium salts. The hydrochloride salts are particularly preferred. The hydrates of the compounds according to the invention, which can be obtained e.g. by crystallization from aqueous solution, are also preferred.

All the compounds according to the invention contain at least one center of asymmetry, namely the C-2 atom identified with an asterisk (*) in the vicinity of the pyrrolidine N atom in formula (1*):

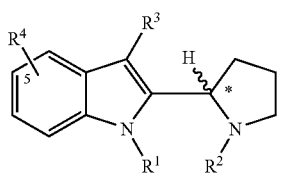

I*

The compounds of the general formula (I) according to the invention can therefore be in the form of their racemates, in the form of the pure enantiomers and/or diastereomers or in the form of mixtures of these enantiomers or diastereomers, and in particular both as the substance and as pharmaceutically acceptable salts or solvates of these compounds. The mixtures can be in any desired mixture ratio of the stereoisomers. The compounds of the general formula (I) are preferably in the form of enantiomerically pure compounds.

Preferred compounds of the general formula (I) are those in which $R^1$ denotes H, alkyl, cycloalkyl or alkyl-cycloalkyl;
$R^2$ denotes C(=O)—$R^{20}$ or $SO_2$—$R^{21}$;
$R^3$ denotes aryl;
$R^4$ denotes H, F, Cl, Br, I, —CN, $OR^{40}$, alkyl, cycloalkyl or $NO_2$, in each case in the 5-position of the indole ring;
$R^{20}$ denotes alkyl, cycloalkyl, alkyl-cycloalkyl, aryl, alkyl-aryl, heterocyclyl or alkyl-heterocyclyl;
$R^{21}$ denotes alkyl, aryl, alkyl-aryl, heterocyclyl or alkyl-heterocyclyl; and
$R^{40}$ denotes H, alkyl, cycloalkyl, alkyl-cycloalkyl, aryl or alkyl-aryl.

Particularly preferred compounds of the general formula (I) are those wherein $R^1$ denotes H or alkyl;
$R^2$ denotes C(=O)—$R^{20}$ or $SO_2$—$R^{21}$;
$R^3$ denotes phenyl;
$R^4$ denotes H, F, Cl, Br or I, in each case in the 5-position of the indole ring;
$R^{20}$ denotes $C_{1-8}$-alkanyl, $C_{2-8}$-alkenyl, $C_{1-4}$-alkanyl-$CO_2$—$C_{1-4}$-alkyl, $C_{1-4}$-alkanyl-O—$R^{202}$, $C_{1-4}$-alkanyl-$NR^{203}R^{204}$, $C_{3-8}$-cycloalkyl, 1-adamantyl, 2-adamantyl, —($C_{1-3}$-alkyl)-$C_{3-8}$-cycloalkyl, aryl$^1$, aryl$^2$, $C_{1-4}$-alkanyl-aryl$^3$, $C_{2-4}$-alkenyl-aryl$^4$; or unsubstituted or substituted furanyl, pyrazolyl, isoxazolyl or pyridinyl; or 4,7,7-trimethyloxabicyclo [2.2.1]heptan-3-one, —$CH_2$-imidazolidine-2,4-dione;
$R^{21}$ denotes aryl$^5$, unsubstituted or substituted thienyl or represents

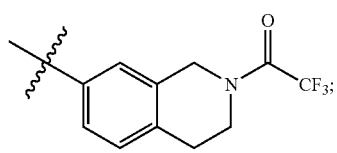

$R^{202}$ denotes H, $C_{1-4}$-alkanyl, $C_{1-4}$-alkanyl-OH, $C_{1-4}$-alkanoyl-O—$C_{1-4}$-alkanyl or aryl;
$R^{203}$ and $R^{204}$ independently of one another denote $C_{1-6}$-alkyl or, with the N atom, form a 5-, 6- or 7-membered saturated heterocyclyl;

aryl$^1$ represents

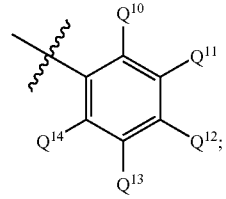

aryl$^2$ represents

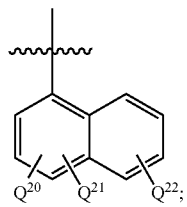

aryl$^3$ represents

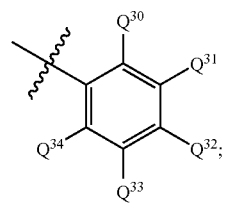

aryl$^4$ represents

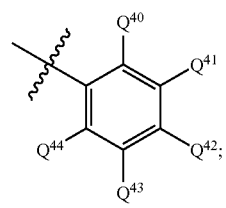

aryl$^5$ represents

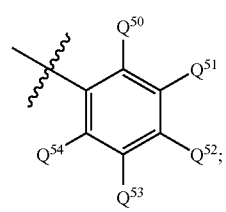

$Q^{10}$, $Q^{11}$, $Q^{12}$, $Q^{13}$, $Q^{14}$, $Q^{20}$, $Q^{21}$, $Q^{22}$, $Q^{30}$, $Q^{31}$, $Q^{32}$, $Q^{33}$, $Q^{34}$, $Q^{40}$, $Q^{41}$, $Q^{42}$, $Q^{43}$, $Q^{44}$, $Q^{50}$, $Q^{51}$, $Q^{52}$, $Q^{53}$ and $Q^{54}$ independently of one another denote H, F, Cl, Br, I, —CN, —NO$_2$, $C_{1-4}$-alkyl, OH, O—$C_{1-4}$-alkyl, SH or S—$C_{1-4}$-alkyl.

Very particularly preferred substituted 2-pyrrolidin-2-yl-1H-indole compounds are those in which $R^1$ denotes H, methyl, but-2-yne or diethylaminoethyl;
$R^2$ denotes C(=O)—$R^{20}$ or SO$_2$—$R^{21}$;
$R^3$ denotes phenyl;
$R^4$ denotes 5-H or 5-Cl;
$R^{20}$ denotes methyl, ethyl, n-propyl, n-butyl, 1-methylpropyl, 2-methylpropyl, tert-butyl, n-pentyl, 1-methylbutyl, 2,2-dimethylpropyl, 1-propylbutyl, 1-ethylpentyl, prop-1-enyl, prop-2-enyl, but-1-enyl, but-2-enyl, but-3-enyl, —(CH$_2$)$_2$—CO$_2$-methyl, —(CH$_2$)$_2$—CO$_2$-ethyl, —CH$_2$—O—CH$_3$, —CH$_2$—O—(CH$_2$)$_2$—O—CH$_3$, —CH$_2$—O-phenyl, —CH$_2$—O-(4-chlorophenyl), —CH(CH$_3$)—O-phenyl, —(CH$_2$)$_3$—O-phenyl, dimethylaminomethyl, cyclopropyl, cyclobutyl, cyclopentyl, cyclohexyl, 1-adamantyl, —CH$_2$-cyclopropyl, —CH$_2$-cyclopentyl, aryl$^1$, 1-naphthyl, CH$_2$-aryl$^3$, —CH(C$_2$H$_5$)-aryl$^3$, —CH=CH-aryl$^4$, furan-2-yl, furan-3-yl, 5-tert-butyl-2-methyl-furan-3-yl, 2,5-dimethyl-furan-3-yl, pyrazol-4-yl, pyrazol-5-yl, 1-tert-butyl-3-methyl-pyrazol-5-yl, 1-phenyl-3-propyl-pyrazol-4-yl, isoxazol-3-yl, isoxazol-4-yl, isoxazol-5-yl, 5-methyl-4-(2-chlorophenyl)-isoxazol-3-yl, 5-methyl-3-(2-chloro-6-fluorophenyl)-isoxazol-4-yl, pyridin-2-yl, pyridin-3-yl, pyridin-4-yl, 2-chloropyridin-3-yl, 6-chloropyridin-3-yl, 2-(CH$_3$—S—)-pyridin-3-yl, 2-methyl-6-trifluoromethyl-pyridin-3-yl, 4,7,7-trimethyloxabicyclo [2.2.1]heptan-3-one or —CH$_2$-imidazolidine-2,4-dione;

$R^{21}$ denotes aryl$^5$, thien-2-yl, thien-3-yl or 5-chloro-thien-2-yl or represents

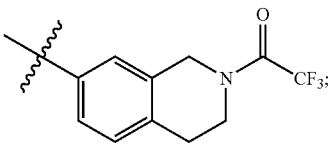

aryl$^1$ represents

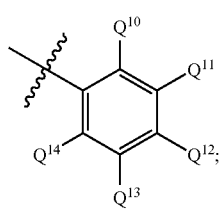

aryl$^3$ represents

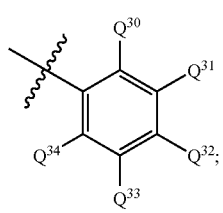

aryl$^4$ represents

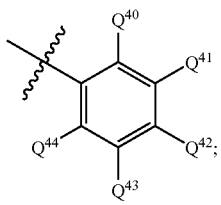

aryl$^5$ represents

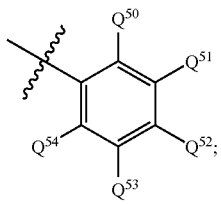

$Q^{10}$, $Q^{11}$, $Q^{12}$, $Q^{13}$ and $Q^{14}$ independently of one another denote H, F, Cl, Br, —NO$_2$, methyl, trifluoromethyl, ethyl, n-propyl, 1-methylethyl, O—CH$_3$, O—CF$_3$, —O—C$_2$H$_5$, S—CH$_3$ or S—CF$_3$;

$Q^{30}$, $Q^{31}$, $Q^{32}$, $Q^{33}$ and $Q^{34}$ independently of one another denote H, Cl or O—CH$_3$;

$Q^{40}$, $Q^{41}$, $Q^{42}$, $Q^{43}$ and $Q^{44}$ independently of one another denote H, Cl, CH$_3$ or CF$_3$; and $Q^{50}$, $Q^{51}$, $Q^{52}$, $Q^{53}$ and $Q^{54}$ independently of one another denote H, F, Cl, Br, methyl, ethyl, n-propyl, 1-methylethyl, O—CH$_3$, O—CF$_3$, O—CH$_2$CH$_3$, O—CH$_2$CH$_2$CH$_3$, O—CH$_2$CH$_2$CH$_2$CH$_3$.

The most preferred compounds of the general formula (I) according to the invention include those wherein $R^1$ denotes H, methyl, but-2-yne or diethylaminoethyl;
$R^2$ denotes C(=O)—$R^{20}$ or SO$_2$—$R^{21}$;
$R^3$ denotes phenyl;
$R^4$ denotes 5-H or 5-Cl;
$R^{20}$ denotes n-propyl, n-butyl, n-pentyl, 1-methylbutyl, 2,2-dimethylpropyl, 1-propylbutyl, 1-ethylpentyl, but-3-enyl, —(CH$_2$)$_2$—CO$_2$-methyl, —(CH$_2$)$_2$—CO$_2$-ethyl, —CH$_2$—O—CH$_3$, —CH$_2$—O—(CH$_2$)$_2$—O—CH$_3$, —CH$_2$—O-phenyl, —CH$_2$—O-(4-chlorophenyl), —CH(CH$_3$)—O-phenyl, —(CH$_2$)$_3$—O-phenyl, dimethylaminomethyl, cyclopropyl, cyclobutyl, cyclohexyl, 1-adamantyl, —CH$_2$-cyclopentyl, 4-fluorophenyl, 4-chlorophenyl, 2-bromophenyl, 3-bromophenyl, 2,3-difluorophenyl, 3-fluoro-4-trifluoromethylphenyl, 3-fluoro-6-trifluoromethylphenyl, 3-fluoro-4-methylphenyl, 3,5-difluorophenyl, 2-chloro-4-nitrophenyl, 2-chloro-5-trifluoromethylphenyl, 4-bromo-3-methylphenyl, 2,3-difluoro-4-methylphenyl, 2,6-difluoro-3-methylphenyl, 2,3,4,5,6-pentafluorophenyl, 4-nitrophenyl, 4-methyl-3-nitrophenyl, 3-methylphenyl, 4-methylphenyl, 2,3-dimethylphenyl, 3-trifluoromethylphenyl, 2,5-trifluoromethylphenyl, 3,5-trifluoromethylphenyl, 4-ethylphenyl, 4-n-propylphenyl, 3-methoxyphenyl, 3,5-dimethoxyphenyl, 3-trifluoromethoxyphenyl, 4-trifluoromethoxyphenyl, 2-ethoxyphenyl, 4-ethoxyphenyl, 4-S—CF$_3$-phenyl, benzyl, 4-chlorobenzyl, 3-methoxybenzyl, 2,5-dimethoxybenzyl, —CH(C$_2$H$_5$)-phenyl, —CH=CH-(2-chlorophenyl), —CH=CH-(3-trifluoromethylphenyl), furan-2-yl, 5-tert-butyl-2-methyl-furan-3-yl, 2,5-dimethyl-furan-3-yl, 1-tert-butyl-3-methyl-pyrazol-5-yl, 1-phenyl-3-propyl-pyrazol-4- yl, isoxazol-5-yl, 5-methyl-4-(2-chlorophenyl)-isoxazol-3-yl, 5-methyl-3-(2-chloro-6-fluorophenyl)-isoxazol-4-yl, pyridin-2-yl, 2-chloropyridin-3-yl, 6-chloropyridin-3-yl, 2-(CH$_3$—S—)-pyridin-3-yl, 2-methyl-6-trifluoromethyl-pyridin-3-yl, 4,7,7-trimethyloxabicyclo[2.2.1]heptan-3-one or —CH$_2$-imidazolidine-2,4-dione; and R$^{21}$ denotes 3-chloro-4-fluorophenyl, 2-chlorophenyl, 4-chlorophenyl, 3-chloro-2-methylphenyl, 3-bromophenyl, 2,3,5,6-tetramethylphenyl, 4-n-butylphenyl, 4-methoxyphenyl, 2,5-dimethoxyphenyl, 4-trifluoromethoxyphenyl, 4-(n-butoxy)-phenyl, thien-2-yl, 5-chlorothien-2-yl or represents

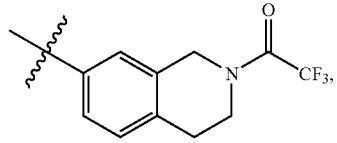

in particular those substituted 2-pyrrolidin-2-yl-1H-indole compounds are chosen from the group which includes:
{2-[5-chloro-1-(2-diethylamino-ethyl)-3-phenyl-1H-indol-2-yl]-pyrrolidin-1-yl}-furan-2-yl-methanone;
4-{2-[5-chloro-1-(2-diethylamino-ethyl)-3-phenyl-1H-indol-2-yl]-pyrrolidin-1-yl}-4-oxo-butyric acid ethyl ester;
{2-[5-chloro-1-(2-diethylamino-ethyl)-3-phenyl-1H-indol-2-yl]-pyrrolidin-1-yl}-(4-fluoro-phenyl)-methanone;
{2-[5-chloro-1-(2-diethylamino-ethyl)-3-phenyl-1H-indol-2-yl]-pyrrolidin-1-yl}-cyclobutyl-methanone;
{2-[5-chloro-1-(2-diethylamino-ethyl)-3-phenyl-1H-indol-2-yl]-pyrrolidin-1-yl}-(6-chloro-pyridin-3-yl)-methanone;
1-{2-[5-chloro-1-(2-diethylamino-ethyl)-3-phenyl-1H-indol-2-yl]-pyrrolidin-1-yl}-hexan-1-one;
{2-[5-chloro-1-(2-diethylamino-ethyl)-3-phenyl-1H-indol-2-yl]-pyrrolidin-1-yl}-(3,5-dimethoxy-phenyl)-methanone;
{2-[5-chloro-1-(2-diethylamino-ethyl)-3-phenyl-1H-indol-2-yl]-pyrrolidin-1-yl}-(4-ethoxy-phenyl)-methanone;
1-[2-(5-chloro-1-methyl-3-phenyl-1H-indol-2-yl)-pyrrolidin-1-yl]-2-(2-methoxy-ethoxy)-ethanone;
[2-(5-chloro-1-methyl-3-phenyl-1H-indol-2-yl)-pyrrolidin-1-yl]-cyclopropyl-methanone; and
1-[2-(1-but-2-ynyl-5-chloro-3-phenyl-1H-indol-2-yl)-pyrrolidin-1-yl]-2-methoxy-ethanone.

The present invention also relates to processes for the preparation of the compounds corresponding to general formula (I) according to the invention.

Substituted 2-pyrrolidin-2-yl-1H-indole compounds corresponding to formula (I) wherein
R$^1$ denotes H, alkyl, cycloalkyl, alkyl-cycloalkyl, alkyl-aryl or alkyl-heterocyclyl;
R$^2$ denotes alkyl, cycloalkyl, alkyl-cycloalkyl, alkyl-aryl, alkyl-heterocyclyl, C(=O)—R$^{20}$ or SO$_2$—R$^{21}$;
R$^3$ denotes alkyl, aryl or heterocyclyl;
R$^4$ denotes H, F, Cl, Br, I, —CN, OR$^{40}$, alkyl, cycloalkyl or NO$_2$;
R$^{20}$ denotes alkyl, cycloalkyl, alkyl-cycloalkyl, aryl, alkyl-aryl, heterocyclyl, alkyl-heterocyclyl, OR$^{200}$ or NHR$^{201}$;
R$^{21}$ denotes alkyl, aryl, alkyl-aryl, heterocyclyl or alkyl-heterocyclyl;
R$^{40}$ denotes H, alkyl, cycloalkyl, alkyl-cycloalkyl, aryl or alkyl-aryl;
R$^{200}$ denotes alkyl, cycloalkyl, alkyl-cycloalkyl, aryl, alkyl-aryl, heterocyclyl or alkyl-heterocyclyl; and
R$^{201}$ denotes alkyl, aryl, alkyl-aryl, heterocyclyl or alkyl-heterocyclyl;

can thus be prepared by a procedure in which, in a process step (A), a 2-pyrrolidin-2-yl-1H-indole compound corresponding to general formula (II)

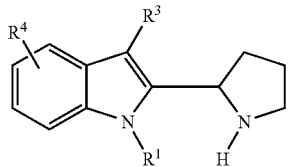

wherein
R$^1$, R$^3$ and R$^4$ are as defined above, is reacted with a compound corresponding to general formula (III)

R$^2$-Hal    III wherein
R$^2$ denotes alkyl, cycloalkyl, alkyl-cycloalkyl, alkyl-aryl, alkyl-heterocyclyl, C(=O)—R$^{20}$ or SO$_2$—R$^{21}$; and
Hal represents chlorine or bromine.

In general, the halide (III) is reacted in excess with the compound corresponding to formula (II), preferably with 1.05 to 1.5 equivalents of (III) (based on (II)). The indole compound (II) is conventionally initially introduced into the reaction vessel in a suitable solvent, preferably a halogenated organic solvent, e.g. methylene chloride, and the halide (III) is added. The reaction is carried out at 0° C. to 150° C., preferably at 20° C. to 40° C., and lasts between 10 min and 12 h. The reaction also proceeds in good yields with substitution of the pyrrolidine N hydrogen by R$^2$ if R$^1$ in formula (II) also denotes H; the pyrrolidine nitrogen proves to be more basic and thus substantially more reactive than the indole nitrogen, so that prior protection of the indole nitrogen with a suitable protective group is indeed possible but not necessary. If R$^2$ denotes C(=O)—R$^{20}$ or SO$_2$—R$^{21}$ in particular, it is advantageous to employ the corresponding acid halide (Hal=Cl in R$^2$-Hal (III)) as the compound (III), and in particular preferably in an amount of approx. 1.05 equivalents (based on the indole (II)); the reaction with the indole (II) here is preferably carried out in the presence of approx. 1.1 equivalents of triethylamine and catalytic amounts (0.01 to 0.1 equivalent) of DMAP (4-dimethylaminopyridine) in methylene chloride as the solvent.

Compounds corresponding to formula (I) according to the invention wherein
R$^1$ and R$^2$ denote H;
R$^3$ denotes alkyl, aryl or heterocyclyl;
R$^4$ denotes H, F, Cl, Br, I, —CN, OR$^{40}$, alkyl, cycloalkyl or NO$_2$; and
R$^{40}$ denotes H, alkyl, cycloalkyl, alkyl-cycloalkyl, aryl or alkyl-aryl;
are obtained in a process step (B) by reaction of a 2-pyrrolidin-2-yl-1H-indole compound corresponding to formula (IV)

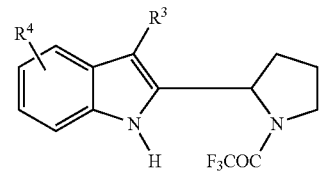

wherein

R³ and R⁴ are as defined above;

with potassium carbonate or sodium hydroxide. The base is preferably employed here as an aqueous solution and in excess.

Compounds corresponding to formula (I) according to the invention wherein

R¹ denotes alkyl, cycloalkyl, alkyl-cycloalkyl, alkyl-aryl or alkyl-heterocyclyl (i.e. is not H);

R² denotes H;

R³ denotes alkyl, aryl or heterocyclyl;

R⁴ denotes H, F, Cl, Br, I, —CN, OR⁴⁰, alkyl, cycloalkyl or NO₂; and

R⁴⁰ denotes H, alkyl, cycloalkyl, alkyl-cycloalkyl, aryl or alkyl-aryl;

are prepared according to the invention in a process step (C) by reaction of a 2-pyrrolidin-2-yl-1H-indole compound corresponding to formula (V)

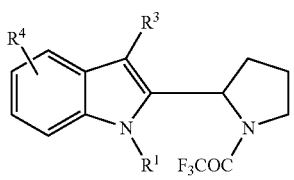

V wherein

R¹, R³ and R⁴ are as defined above;

with potassium carbonate or sodium hydroxide. The base (i.e. K₂CO₃ or NaOH) is preferably employed here as an aqueous solution and in excess.

2-Pyrrolidin-2-yl-1H-indole derivatives of the general formula (V) where

R¹ is alkyl, cycloalkyl, alkyl-cycloalkyl, alkyl-aryl or alkyl-heterocyclyl;

R³ is alkyl, aryl or heterocyclyl;

R⁴ is H, F, Cl, Br, I, —CN, OR⁴⁰, alkyl, cycloalkyl or NO₂; and

R⁴⁰ is H, alkyl, cycloalkyl, alkyl-cycloalkyl, aryl or alkyl-aryl;

are obtained in a process step (D) starting from a 2-pyrrolidin-2-yl-1H-indole derivative of the general formula (IV)

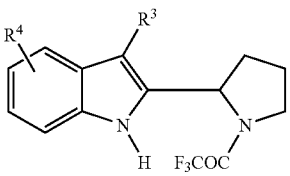

IV wherein

R³ and R⁴ are as defined above;

by reaction with a compound of the general formula (VI)

R¹-Hal    VI wherein

R¹ is as defined above and Hal denotes Cl, Br or I. The halide (VI) is in general employed here in excess. To improve the rate or conversion of the reaction, it is prefer-
able to carry out this reaction in the presence of a slight excess (e.g. 1.05 to 1.2 equivalents) of a strong base, e.g. sodium hydride, in particular in an ethereal solvent, such as tetrahydrofuran (THF).

It is furthermore preferable to carry out process steps (D) and (C) as a two-stage reaction sequence starting from a compound of the general formula (IV) as defined above, via the corresponding compound (V), to give the compound of the formula (I) wherein R¹ denotes alkyl, cycloalkyl, alkyl-cycloalkyl, alkyl-aryl or alkyl-heterocyclyl; R² denotes H; R³ denotes alkyl, aryl or heterocyclyl; R⁴ denotes H, F, Cl, Br, I, —CN, OR⁴⁰, alkyl, cycloalkyl or NO₂; and R⁴⁰ denotes H, alkyl, cycloalkyl, alkyl-cycloalkyl, aryl or alkyl-aryl. This can optionally be followed by process steps (A) as a further reaction step, in which case compounds of the formula (I) where R² is not H (i.e. is alkyl, cycloalkyl, alkyl-cycloalkyl, alkyl-aryl, alkyl-heterocyclyl, C(=O)—R²⁰ or SO₂—R²¹) are then obtained.

For the preparation of compounds of the formula (I) where R¹ is H and R² is alkyl, cycloalkyl, alkyl-cycloalkyl, alkyl-aryl, alkyl-heterocyclyl, C(=O)—R²⁰ or SO₂—R²¹, it is furthermore preferable, in a two-stage reaction sequence, to convert a compound of the formula (IV) into a compound of the formula (I) where R¹ and R² are H in a process step (B), in order subsequently to react this with a suitable halide R²-Hal (III) in a process step (A) to give the desired compound where R² is not H.

The trifluoroacetyl-protected compounds of the formula (IV) according to the invention are accessible in accordance with processes known from the literature ((A. Fürstner, A. Hupperts, *J. Am. Chem. Soc.* (1995), 117, 4468-4475; A Fürstner et al., *Org. Synth.* (1999), 76, 142-150): The aniline derivatives, which are obtainable commercially or by standard synthesis methods known to the expert, of the general formula (VIII)

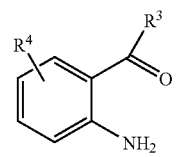

VIII wherein

R³ denotes alkyl, aryl or heterocyclyl;

R⁴ denotes H, F, Cl, Br, I, —CN, OR⁴⁰, alkyl, cycloalkyl or NO₂; and

R⁴⁰ denotes H, alkyl, cycloalkyl, alkyl-cycloalkyl, aryl or alkyl-aryl, is [sic] converted in a process step (E) by reaction with N-trifluoroacetylproline alkyl esters (VII)

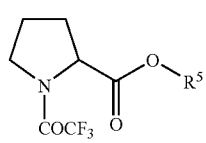

VII wherein R⁵ denotes alkyl, in particular methyl or ethyl, into the corresponding N-acylated compound of the formula (IX)

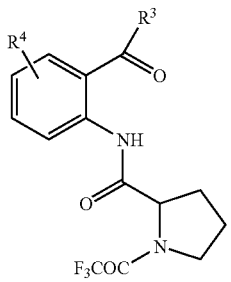

IX wherein

R³ and R⁴ are as defined above for formula (VIII).

(The trifluoroacetylproline alkyl esters (VII) are readily accessible from the corresponding proline alkyl esters and a suitable trifluoroacetic acid derivative, e.g. trifluoroacetyl chloride.) Compound (IX) is then subjected to a McMurry coupling in a process step (F) under reaction conditions which correspond to the conditions described by Fürstner et al. (A. Fürstner, A. Hupperts. *J. Am. Chem. Soc.* (1995), 117, 4468-4475; A Fürstner et al., *Org. Synth.* (1999), 76, 142-150). A suitable procedure envisages e.g. the use of approx. 2 equivalents of titanium trichloride and approx. 4 equivalents of zinc dust—in each case based on 1 equivalent of ketoamide (IX)—in acetonitrile. It is also possible to suspend the ketoamide (IX) with 10 mol % TiCl₃ and 4 equivalents of zinc dust in CH₃CN, subsequently to add 4 equivalents of trimethylsilyl chloride (TMSCl) and to heat the mixture under reflux, e.g. for 15 min to 2 h. After conventional working up, this gives the desired compound of the formula (IV) in good yields. If enantiomerically pure (R)— or (S)—N-trifluoroacetylproline alkyl esters (VII) are employed in process step (E), the reaction products of process steps (E) and (F) are obtained in a high stereoisomer purity.

The individual process steps according to the invention are preferably combined as follows to give multi-stage syntheses:

Starting from (IV): 1.(B)→2.(A) or 1.(D)→2.(C) and optionally→3.(A).

Starting from (VIII): 1.(E)→2.(F)→3.(B)→4.(A) or 1.(E)→2.(F)→3.(D)→4.(C) and optionally→5.(A).

Here also, the corresponding reaction products are obtained in a high stereoisomer purity if reaction step (E) is carried out with enantiomerically pure trifluoroacetylproline alkyl esters (VII).

The compounds of the general structure (I) according to the invention (and of the formulae (II), (IV) and (V)) can be isolated both as the substance and as a salt. The substances of the general structure (I) are conventionally obtained after the reaction according to the process described above and subsequent conventional working up. The compounds obtained in this way can then be converted into the corresponding salt, for example, by addition of an inorganic or organic acid, preferably hydrochloric acid, hydrobromic acid, sulfuric, acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid. The salts formed are, inter alia, hydrochlorides, hydrobromides, phosphates, carbonates, bicarbonates, formates, acetates, oxalates, succinates, tartrates, fumarates, citrates and glutamates. Where the compounds of the general formula (I) are acids, in particular carboxylic acids, the salt formation can be brought about by addition of a base, e.g. sodium hydroxide, NaHCO₃ or sodium carbonate; for the (carboxylic) acids, the formation of the sodium salt is preferred in particular. The particularly preferred hydrochloride formation can also be brought about, in particular, by adding trimethylsilyl chloride (TMSCl) to the base (I) dissolved in a suitable organic solvent. The formation of sodium salts can be carried out e.g. by titration of the compound (I), dissolved in a suitable solvent, for example a water/methanol mixture, with sodium hydroxide solution.

If the compounds of the general formula (I) are obtained as racemates or as mixtures of their various stereoisomers, in particular enantiomers and/or diastereomers, in the preparation process according to the invention, these mixtures can be separated by processes which are well-known in the prior art. Suitable methods are, inter alia, chromatographic separation processes, in particular liquid chromatography processes under normal or increased pressure, preferably MPLC and HPLC processes, and fractional crystallization processes. Individual enantiomers can be separated from one another here in particular e.g. by means of HPLC on a chiral phase or by means of crystallization of diastereomeric salts formed with chiral acids, for example (+)-tartaric acid, (−)-tartaric acid or (+)-10-camphorsulfonic acid, or—if they are acids—with chiral bases, for example brucine or (−)-ephedrine.

The substituted 2-pyrrolidin-2-yl-1H-indole derivatives of the formula (I) according to the invention have proved to be potent NOS inhibitors. The present invention therefore also provides a medicament comprising at least one compound of the general formula (I) as defined above, wherein the compound (I) is in the form of the racemate, the pure stereoisomers, in particular enantiomers or diastereomers, or in the form of mixtures of the stereoisomers, in particular of the enantiomers or diastereomers, in any desired mixture ratio, in the form shown in formula (I) or in the form of their acids or their bases or in the form of their physiologically acceptable salts, or in the form of their solvates, in particular the hydrates. The compound of the formula (I) is preferably present in the medicament according to the invention in the form of the hydrochloride salt.

The present invention furthermore provides the use of a substituted 2-pyrrolidin-2-yl-1H-indole derivative of the formula (I) as defined above in the form of the racemate, the pure stereoisomers, in particular enantiomers or diastereomers, or in the form of mixtures of the stereoisomers, in particular of the enantiomers or diastereomers, in any desired mixture ratio, in the form shown or in the form of their acids or their bases or in the form of their physiologically acceptable salts, or in the form of their solvates, in particular the hydrates, for the preparation of a medicament for inhibition of NO synthase, and in particular for the preparation of a medicament for prophylaxis and therapy of migraine.

On the basis of their NO synthase-inhibiting properties, the substituted 2-pyrrolidin-2-yl-1H-indole derivatives of the formula (I) as defined above are also suitable for the preparation of a medicament for prophylaxis and/or therapy of septic shock, multiple sclerosis, Parkinson's disease, Alzheimer's disease, Huntington's disease, inflammations, inflammation pain, cerebral ischaemia, diabetes, meningitis, arteriosclerosis and/or for wound healing.

The medical preparations and medicaments according to the invention are conventionally prepared as pharmaceutical compositions which comprise at least one compound of the general formula (I), and in particular as the substance and/or as a pharmaceutically acceptable salt and/or solvate, and one or more pharmaceutical auxiliary substances.

The medical preparations, medicaments and pharmaceutical compositions according to the invention can be present and administered as liquid, semi-solid or solid medicament forms and in the form of e.g. injection solutions, drops, juices, syrups, sprays, suspensions, granules, tablets, pellets, patches, capsules, plasters, suppositories, ointments, creams, lotions, gels, emulsions or aerosols and, in addition to at least one compound of the general structure (I) according to the invention, comprise pharmaceutical auxiliary substances, such as e.g. carrier materials, fillers, solvents, diluents, surface-active substances, dyestuffs, preservatives, disintegrating agents, lubricants, slip agents, flavours and/or binders, depending on the pharmaceutical form. These auxiliary substances can be, for example: water, ethanol, 2-propanol, glycerol, ethylene glycol, propylene glycol, polyethylene glycol, polypropylene glycol, glucose, fructose, lactose, sucrose, dextrose, molasses, starch, modified starch, gelatines, sorbitol, inositol, mannitol, microcrystalline cellulose, methylcellulose, carboxymethylcellulose, cellulose acetate, shellac, cetyl alcohol, polyvinylpyrrolidone, paraffins, waxes, pharmaceutically acceptable naturally occurring and synthetic gums, gum acacia, alginates, dextran, saturated and unsaturated fatty acids, stearic acid, magnesium stearate, zinc stearate, glyceryl stearate, sodium lauryl sulfate, edible oils, sesame oil, coconut oil, groundnut oil, soya bean oil, lecithin, sodium lactate, polyoxyethylene and -propylene fatty acid esters, sorbitan fatty acid esters, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulfate, zinc sulfate, calcium sulfate, potash, calcium phosphate, dicalcium phosphate, potassium bromide, potassium iodide, talc, kaolin, pectin, crospovidone, agar and bentonite.

The choice of auxiliary substances and the amounts thereof to be employed depends on whether the medicament is to be administered orally, subcutaneously, parenterally, intravenously, intraperitoneally, intradermally, intramuscularly, intranasally, buccally, rectally or locally, for example on infections on the skin, the mucous membranes and on the eyes. Formulations in the form of tablets, coated tablets, capsules, granules, drops, juices and syrups are suitable, inter alia, for oral administration, and solutions, suspensions, easily reconstitutable dry formulations as well as sprays are suitable for parenteral, topical and inhalatory administration. Compounds of the general structure (I) according to the invention in a depot in dissolved form or in a patch, optionally with the addition of agents which promote penetration through the skin, are suitable formulations for percutaneous administration. Formulation forms which can be used orally or percutaneously can release the compounds of the general structure (I) according to the invention in a delayed manner.

The preparation of the medicaments and pharmaceutical compositions according to the invention is carried out with the aid of means, devices, methods and processes which are well-known in the prior art of pharmaceutical formulation, such as are described, for example, in "Remington's Pharmaceutical Sciences", ed. A. R. Gennaro, 17th ed., Mack Publishing Company, Easton, Pa. (1985), in particular in part 8, chapter 76 to 93.

Thus e.g. for a solid formulation, such as a tablet, the active compound of the medicament, i.e. a compound of the general structure (I) or one of its pharmaceutically acceptable salts, can be mixed with a pharmaceutical carrier, e.g. conventional tablet constituents, such as maize starch, lactose, sucrose, sorbitol, talc, magnesium stearate, dicalcium phosphate or gum, and pharmaceutical diluents, such as e.g. water, in order to form a solid preformulation composition which comprises a compound according to the invention or a pharmaceutically acceptable salt thereof in homogeneous distribution. Homogeneous distribution is understood here as meaning that the active compound is distributed uniformly over the entire preformulation composition, so that this can readily be divided into unit dose forms having the same action, such as tablets, pills or capsules. The solid preformulation composition is then divided into unit dose forms. The tablets or pills of the medicament according to the invention or of the compositions according to the invention can also be coated, or compounded in another manner, to provide a dose form with delayed release. Suitable coating compositions are, inter alia, polymeric acids and mixtures of polymeric acids with materials such as e.g. shellac, cetyl alcohol and/or cellulose acetate.

The invention also provides a method for treatment of disease states in a mammal and/or human which can be influenced positively by inhibition of NO synthase, in particular migraine, septic shock, multiple sclerosis, Parkinson's disease, Alzheimer's disease, Huntington's disease, inflammations, inflammation pain, cerebral ischaemia, diabetes, meningitis, arteriosclerosis and/or for wound healing, wherein the method is characterized in that a therapeutically active amount of a compound of the general formula (I) according to the invention in the form shown or in the form of its acids or its bases or in the form of the pharmaceutically acceptable, in particular physiologically acceptable salts, or in the form of its solvates, in particular the hydrates, optionally in the form of its racemates, its pure stereoisomers, in particular enantiomers or diastereomers, or in the form of mixtures of the stereoisomers, in particular of the enantiomers or diastereomers, in any desired mixture ratio, is administered.

The amount of active compound to be administered to the patient varies and depends on the weight, the age and the disease history of the patient, as well as on the mode of administration, the indication and the severity of the disease. 0.1 to 5,000 mg/kg, in particular 1 to 500 mg/kg, preferably 2 to 250 mg/kg of body weight of at least one compound of the general formula (I) according to the invention are conventionally administered.

EXAMPLES

Preparation of Substituted
2-pyrrolidin-2-yl-1H-indole Derivatives of the
Formula (I) According to the Invention (General
Working Instructions 1)

1.1 molar equivalents of the aniline derivative (VIII) are dissolved in tetrahydrofuran (about 2 ml per mmol of amine). 2.2 molar equivalents of n-butyllithium solution (1.6 mol/l in hexane) are then added dropwise, while cooling with an ice bath, and the mixture is subsequently stirred for one hour. The reaction solution is then cooled with the aid of a dry ice bath and a solution of the N-trifluoroacetylproline ethyl ester (VII) (1 molar equivalent) in tetrahydrofuran (about 0.5 ml per mmol of ester) is added dropwise. The mixture is subsequently stirred for one hour, while cooling with dry ice, and is warmed up overnight. After addition of half-saturated ammonium chloride solution (about 2.5 ml per mmol of ester), the mixture is extracted several times with ether, ethyl acetate and methylene chloride. The extracts obtained in this way are combined, dried over sodium sulfate, filtered and concentrated to dryness in vacuo under a pressure of 500 to 20 mbar. The ketoamide (IX) formed is suspended with 10 mol % $TiCl_3$ and 4 equivalents of zinc dust in acetonitrile. 4 equivalents of TMSCl are added and the mixture is heated under reflux for 30 min. It is cooled to room temperature, diluted with ethyl acetate and filtered over silica gel. The filtrate is concentrated to dryness in vacuo under a pressure of 500 to 20 mbar and purified over silica gel with n-hexane/ethyl acetate 9:1.

For the purpose of the formation of the compound (V) (where $R^1 \neq H$), the indole derivative (IV) formed is reacted with 1.05 equivalents of NaH and 1.1 equivalents of alkyl chloride, bromide or iodide in THF.

The $COCF_3$ protective group is split off with the aid of aqueous $K_2CO_3$ or NaOH solution.

Substances of the general formula (II) (where $R^2$=H) are converted into the corresponding compounds (I) (where $R^2 \neq H$) with 1.05 equivalents of carboxylic acid chloride, sulfonic acid chloride or alkyl or cycloalkyl chloride in the presence of 1.1 equivalents of triethylamine and catalytic amounts of DMAP in methylene chloride.

The following compounds (table 1) were prepared, by way of example, in accordance with the general working instructions and identified by means of NMR and/or MS:

TABLE 1

| Example no. | Compound |
|---|---|
| 1 | (2-Bromo-phenyl)-[2-(3-phenyl-1H-indol-2-yl)-pyrrolidin-1-yl]-methanone |
| 2 | 1-But-2-ynyl-5-chloro-3-phenyl-2-[1-thiophene-2-sulfonyl)-pyrrolidin-2-yl]-1H-indole |
| 3 | 2-Phenyl-1-[2-(3-phenyl-1H-indol-2-yl)-pyrrolidin-1-yl]-butan-1-one |
| 4 | 2-(2,5-Dimethoxy-phenyl)-1-[2-(3-phenyl-1H-indol-2-yl)-pyrrolidin-1-yl]-ethanone |
| 5 | (4-Bromo-3-methyl-phenyl)-[2-(5-chloro-3-phenyl-1H-indol-2-yl)-pyrrolidin-1-yl]-methanone |
| 6 | (3-Methoxy-phenyl)-[2-(3-phenyl-1H-indol-2-yl)-pyrrolidin-1-yl]-methanone |
| 7 | (4-Nitro-phenyl)-[2-(3-phenyl-1H-indol-2-yl)-pyrrolidin-1-yl]-methanone |
| 8 | (4-Chloro-phenyl)-[2-(3-phenyl-1H-indol-2-yl)-pyrrolidin-1-yl]-methanone |
| 9 | {2-[5-Chloro-1-(2-diethylamino-ethyl)-3-phenyl-1H-indol-2-yl]-pyrrolidin-1-yl}-furan-2-yl-methanone |
| 10 | [2-(5-Chloro-3-phenyl-1H-indol-2-yl)-pyrrolidin-1-yl]-(2,3-difluoro-4-methyl-phenyl)-methanone |
| 11 | (2,6-Difluoro-3-methyl-phenyl)-[2-(3-phenyl-1H-indol-2-yl)-pyrrolidin-1-yl]-methanone |
| 12 | 4-{2-[5-Chloro-1-(2-diethylamino-ethyl)-3-phenyl-1H-indol-2-yl]-pyrrolidin-1-yl}-4-oxo-butyric acid ethyl ester |
| 13 | {2-[5-Chloro-1-(2-diethylamino-ethyl)-3-phenyl-1H-indol-2-yl]-pyrrolidin-1-yl}-(4-fluoro-phenyl)-methanone |
| 14 | 2-Phenoxy-1-[2-(3-phenyl-1H-indol-2-yl)-pyrrolidin-1-yl]-propan-1-one |
| 15 | {2-[5-Chloro-1-(2-diethylamino-ethyl)-3-phenyl-1H-indol-2-yl]-pyrrolidin-1-yl}-cyclobutyl-methanone |
| 16 | [2-(1-But-2-ynyl-3-phenyl-1H-indol-2-yl)-pyrrolidin-1-yl]-(2-chloro-5-trifluoromethyl-phenyl)-methanone |
| 17 | {2-[5-Chloro-1-(2-diethylamino-ethyl)-3-phenyl-1H-indol-2-yl]-pyrrolidin-1-yl)-(6-chloro-pyridin-3-yl)-methanone |
| 18 | Pentafluorophenyl-[2-(3-phenyl-1H-indol-2-yl)-pyrrolidin-1-yl]-methanone |
| 19 | 1-[2-(3-Phenyl-1H-indol-2-yl)-pyrrolidin-1-yl]-butan-1-one |
| 20 | 1-{2-[5-Chloro-1-(2-diethylamino-ethyl)-3-phenyl-1H-indol-2-yl]-pyrrolidin-1-yl}-hexan-1-one |
| 21 | 5-Chloro-1-methyl-3-phenyl-2-[1-(thiophene-2-sulfonyl)-pyrrolidin-2-yl]-1H-indole |

TABLE 1-continued

| Example no. | Compound |
|---|---|
| 22 | (2-Chloro-4-nitro-phenyl)-[2-(5-chloro-3-phenyl-1H-indol-2-yl)-pyrrolidin-1-yl]-methanone |
| 23 | (4-Bromo-3-methyl-phenyl)-[2-(3-phenyl-1H-indol-2-yl)-pyrrolidin-1-yl]-methanone |
| 24 | 1-[2-(5-Chloro-3-phenyl-1H-indol-2-yl)-pyrrolidin-1-yl]-pent-4-en-1-one |
| 25 | 2-[1-(3-Bromo-benzylsulfonyl)-pyrrolidin-2-yl]-3-phenyl-1H-indole |
| 26 | {2-[5-Chloro-1-(2-diethylamino-ethyl)-3-phenyl-1H-indol-2-yl]-pyrrolidin-1-yl}-(3,5-dimethoxy-phenyl)-methanone |
| 27 | 4-Oxo-4-[2-(3-phenyl-1H-indol-2-yl)-pyrrolidin-1-yl]-butyric acid methyl ester |
| 28 | {2-[5-Chloro-1-(2-diethylamino-ethyl)-3-phenyl-1H-indol-2-yl]-pyrrolidin-1-yl}-(4-ethoxy-phenyl)-methanone |
| 29 | 5-Chloro-3-phenyl-2-[1-(2,3,5,6-tetramethyl-benzylsulfonyl)-pyrrolidin-2-yl]-1H-indole |
| 30 | (2,5-Bis-trifluoromethyl-phenyl)-[2-(3-phenyl-1H-indol-2-yl)-pyrrolidin-1-yl]-methanone |
| 31 | [2-(1-But-2-ynyl-5-chloro-3-phenyl-1H-indol-2-yl)-pyrrolidin-1-yl]-(3-methoxy-phenyl)-methanone |
| 32 | [2-(1-But-2-ynyl-3-phenyl-1H-indol-2-yl)-pyrrolidin-1-yl]-(2-methylsulfanyl-pyridin-3-yl)-methanone |
| 33 | 1-[2-(5-Chloro-3-phenyl-1H-indol-2-yl)-pyrrolidin-1-yl]-2-phenoxy-ethanone |
| 34 | [3-(2-Chloro-6-fluoro-phenyl)-5-methyl-isoxazol-4-yl]-[2-(5-chloro-3-phenyl-1H-indol-2-yl)-pyrrolidin-1-yl]-methanone |
| 35 | 1-[2-(5-Chloro-1-methyl-3-phenyl-1H-indol-2-yl)-pyrrolidin-1-yl]-2-(2-methoxy-ethoxy)-ethanone |
| 36 | 5-Chloro-3-phenyl-2-[1-(thiopohene-2-sulfonyl)-pyrrolidin-2-yl]-1H-indole |
| 37 | [2-(3-Phenyl-1H-indol-2-yl)-pyrrolidin-1-yl]-(3-trifluoromethoxy-phenyl)-methanone |
| 38 | 5-Chloro-2-[1-(3-chloro-2-methyl-benzylsulfonyl)-pyrrolidin-2-yl]-3-phenyl-1H-indole |
| 39 | 1-[2-(1-But-2-ynyl-5-chloro-3-phenyl-1H-indol-2-yl)-pyrrolidin-1-yl]-pentan-1-one |
| 40 | 5-{2-Oxo-2-[2-(3-phenyl-1H-indol-2-yl)-pyrrolidin-1-yl]-ethyl}-imidazolidine-2,4-dione |
| 41 | [2-(5-Chloro-1-methyl-3-phenyl-1H-indol-2-yl)-pyrrolidin-1-yl]-(3-trifluoromethyl-phenyl)-methanone |
| 42 | (2-tert-Butyl-5-methyl-2H-pyrazol-3-yl)-[2-(5-chloro-3-phenyl-1H-indol-2-yl)-pyrrolidin-1-yl]-methanone |
| 43 | (2,3-Dimethyl-phenyl)-[2-(3-phenyl-1H-indol-2-yl)-pyrrolidin-1-yl]-methanone |
| 44 | [2-(5-Chloro-3-phenyl-1H-indol-2-yl)-pyrrolidin-1-yl]-(3-trifluoromethyl-phenyl)-methanone |
| 45 | [2-(5-Chloro-3-phenyl-1H-indol-2-yl)-pyrrolidin-1-yl]-(4-trifluoromethylsulfanyl-phenyl)-methanone |
| 46 | 5-tert-Butyl-2-methyl-furan-3-yl)-[2-(5-chloro-1H-indol-2-yl)-pyrrolidin-1-yl]-methanone |
| 47 | [2-(5-Chloro-1-methyl-3-phenyl-1H-indol-2-yl)-pyrrolidin-1-yl]-(2-chloro-pyridin-3-yl)-methanone |
| 48 | [2-(5-Chloro-1-methyl-3-phenyl-1H-indol-2-yl)-pyrrolidin-1-yl]-cyclopropyl-methanone |
| 49 | 3-Phenyl-2-[1-(4-trifluoromethoxy-benzylsulfonyl)-pyrrolidin-2-yl]-1H-indole |
| 50 | 2-Methyl-1-[2-(3-phenyl-1H-indol-2-yl)-pyrrolidin-1-yl]-pentan-1-one |
| 51 | 1-But-2-ynyl-2-[1-(4-chloro-benzylsulfonyl)-pyrrolidin-2-yl]-3-phenyl-1H-indole |
| 52 | 1-[2-(5-Chloro-1-methyl-3-phenyl-1H-indol-2-yl)-pyrrolidin-1-yl]-4-phenoxy-butan-1-one |
| 53 | [2-(5-Chloro-3-phenyl-1H-indol-2-yl)-pyrrolidin-1-yl]-(2,3-dimethyl-phenyl)-methanone |
| 54 | [2-(5-Chloro-3-phenyl-1H-indol-2-yl)-pyrrolidin-1-yl]-(3,5-dimethoxy-phenyl)-methanone |
| 55 | [2-(3-Phenyl-1H-indol-2-yl)-pyrrolidin-1-yl]-(4-trifluoromethylsulfanyl-phenyl)-methanone |
| 56 | 1-But-2-ynyl-5-chloro-2-[1-(2-chloro-benzylsulfonyl)-pyrrolidin-2-yl]-3-phenyl-1H-indole |
| 57 | [2-(1-But-2-ynyl-5-chloro-3-phenyl-1H-indol-2-yl)-pyrrolidin-1-yl]-(2-chloro-4-nitro-phenyl)-methanone |
| 58 | [2-(3-Phenyl-1H-indol-2-yl)-pyrrolidin-1-yl]-m-tolyl-methanone |

TABLE 1-continued

| Example no. | Compound |
|---|---|
| 59 | (3,5-Bis-trifluoromethyl-phenyl)-[2-(1-but-2-ynyl-3-phenyl-1H-indol-2-yl)-pyrrolidin-1-yl]-methanone |
| 60 | 1-But-2-ynyl-5-chloro-2-[1-(4-methoxy-benzylsulfonyl)-pyrrolidin-2-yl]-3-phenyl-1H-indole |
| 61 | [2-(1-But-2-ynyl-3-phenyl-1H-indol-2-yl)-pyrrolidin-1-yl]-(2-chloro-4-nitro-phenyl)-methanone |
| 62 | [2-(5-Chloro-1-methyl-3-phenyl-1H-indol-2-yl)-pyrrolidin-1-yl]-(2,3-dimethyl-phenyl)-methanone |
| 63 | 1-But-2-ynyl-5-chloro-2-[1-(2,5-dimethoxy-benzylsulfonyl)-pyrrolidin-2-yl]-3-phenyl-1H-indole |
| 64 | 1-[2-(5-Chloro-1-methyl-3-phenyl-1H-indol-2-yl)-pyrrolidin-1-yl]-2-methyl-pentan-1-one |
| 65 | 2-(4-Chloro-phenoxy)-1-[2-(5-chloro-3-phenyl-1H-indol-2-yl)-pyrrolidin-1-yl]-ethanone |
| 66 | (2-Methyl-6-trifluoromethyl-pyridin-3-yl)-[2-(3-phenyl-1H-indol-2-yl)-pyrrolidin-1-yl]-methanone |
| 67 | 1-[2-(5-Chloro-1-methyl-3-phenyl-1H-indol-2-yl)-pyrrolidin-1-yl]-2-cyclopentyl-ethanone |
| 68 | 2-[1-(4-Butoxy-benzylsulfonyl)-pyrrolidin-2-yl]-1-but-2-ynyl-3-phenyl-1H-indole |
| 69 | (4-Bromo-3-methyl-phenyl)-[2-(5-chloro-1-methyl-3-phenyl-1H-indol-2-yl)-pyrrolidin-1-yl]-methanone |
| 70 | [2-(1-But-2-ynyl-5-chloro-3-phenyl-1H-indol-2-yl)-pyrrolidin-1-yl]-(4-ethyl-phenyl)-methanone |
| 71 | [2-(5-Chloro-1-methyl-3-phenyl-1H-indol-2-yl)-pyrrolidin-1-yl]-(2,3-difluorophenyl)-methanone |
| 72 | 1-[2-(1-But-2-ynyl-3-phenyl-1H-indol-2-yl)-pyrrolidin-1-yl]-3-(3-trifluoromethyl-phenyl)-propenone |
| 73 | 1-[2-(1-But-2-ynyl-5-chloro-3-phenyl-1H-indol-2-yl)-pyrrolidin-1-yl]-2-methoxy-ethanone |
| 74 | 1-[2-(1-But-2-ynyl-5-chloro-3-phenyl-1H-indol-2-yl)-pyrrolidin-1-yl]-3,3-dimethyl-butan-1-one |
| 75 | [2-(1-But-2-ynyl-5-chloro-3-phenyl-1H-indol-2-yl)-pyrrolidin-1-yl]-p-tolyl-methanone |
| 76 | [2-(3-Phenyl-1H-indol-2-yl)-pyrrolidin-1-yl]-(3-trifluoromethyl-phenyl)-methanone |
| 77 | 3-Phenyl-2-[1-(thiophene-2-sulfonyl)-pyrrolidin-2-yl]-1H-indole |
| 78 | [2-(5-Chloro-1-methyl-3-phenyl-1H-indol-2-yl)-pyrrolidin-1-yl]-[3-(2-chloro-phenyl)-5-methyl-isoxazol-4-yl]-methanone |
| 79 | 1-[2-(1-But-2-ynyl-5-chloro-3-phenyl-1H-indol-2-yl)-pyrrolidines-1-carbonyl]-4,7,7-trimethyl-2-oxa-bicyclo[2.2.1]heptan-3-one [sic] |
| 80 | 1-[2-(5-Chloro-1-methyl-3-phenyl-1H-indol-2-yl)-pyrrolidin-1-yl]-2-phenoxy-ethanone |
| 81 | (3-Fluoro-4-trifluoromethyl-phenyl)-[2-(3-phenyl-1H-indol-2-yl)-pyrrolidin-1-yl]-methanone |
| 82 | 1-But-2-ynyl-2-[1-(2-chloro-benzylsulfonyl)-pyrrolidin-2-yl]-3-phenyl-1H-indole |
| 83 | [2-(1-But-2-ynyl-3-phenyl-1H-indol-2-yl)-pyrrolidin-1-yl]-(4-trifluoromethoxy-phenyl)-methanone |
| 84 | [2-(1-But-2-ynyl-3-phenyl-1H-indol-2-yl)-pyrrolidin-1-yl]-(4-propyl-phenyl)-methanone |
| 85 | [2-(1-But-2-ynyl-5-chloro-3-phenyl-1H-indol-2-yl)-pyrrolidin-1-yl]-(3-fluoro-4-methyl-phenyl)-methanone |
| 86 | 1-[2-(1-But-2-ynyl-5-chloro-3-phenyl-1H-indol-2-yl)-pyrrolidin-1-yl]-2-propyl-pentan-1-one |
| 87 | 1-[2-(1-But-2-ynyl-3-phenyl-1H-indol-2-yl)-pyrrolidin-1-yl]-2-phenoxy-propan-1-one |
| 88 | (3-Bromo-phenyl)-[2-(1-but-2-ynyl-5-chloro-3-phenyl-1H-indol-2-yl)-pyrrolidin-1-yl]-methanone |
| 89 | 1-[2-(1-But-2-ynyl-5-chloro-3-phenyl-1H-indol-2-yl)-pyrrolidin-1-yl]-2-(2,5-dimethoxy-phenyl)-ethanone |
| 90 | 1-[2-(1-But-2-ynyl-5-chloro-3-phenyl-1H-indol-2-yl)-pyrrolidin-1-yl]-2-dimethylamino-ethanone |
| 91 | Naphthalen-1-yl-[2-(3-phenyl-1H-indol-2-yl)-pyrrolidin-1-yl]-methanone |
| 92 | [2-(5-Chloro-1-methyl-3-phenyl-1H-indol-2-yl)-pyrrolidin-1-yl]-(4-methyl-3-nitro-phenyl)-methanone |
| 93 | 1-[2-(1-But-2-ynyl-5-chloro-3-phenyl-1H-indol-2-yl)-pyrrolidin-1-yl]-2-(4-chloro-phenoxy)-ethanone |
| 94 | 1-[2-(1-But-2-ynyl-3-phenyl-1H-indol-2-yl)-pyrrolidin-1-yl]-butan-1-one |
| 95 | 1-[2-(1-But-2-ynyl-3-phenyl-1H-indol-2-yl)-pyrrolidin-1-yl]-3-(2-chloro-phenyl)-propenone |
| 96 | (2,5-Bis-trifluoromethyl-phenyl)-[2-(1-but-2-ynyl-5-chloro-3-phenyl-1H-indol-2-yl)-pyrrolidin-1-yl]-methanone |
| 97 | 2-Ethyl-1-[2-(3-phenyl-1H-indol-2-yl)-pyrrolidin-1-yl]-hexan-1-one |
| 98 | [2-(1-But-2-ynyl-3-phenyl-1H-indol-2-yl)-pyrrolidin-1-yl]-(3-trifluoromethyl-phenyl)-methanone |
| 99 | 1-[2-(1-But-2-ynyl-5-chloro-3-phenyl-1H-indol-2-yl)-pyrrolidin-1-yl]-2-(4-chloro-phenyl)-ethanone |
| 100 | [2-(1-But-2-ynyl-3-phenyl-1H-indol-2-yl)-pyrrolidin-1-yl]-(5-fluoro-2-trifluoromethyl-phenyl)-methanone |
| 101 | 1-[2-(1-But-2-ynyl-3-phenyl-1H-indol-2-yl)-pyrrolidin-1-yl]-2-phenyl-ethanone |
| 102 | 1-But-2-ynyl-3-phenyl-2-[1-(4-propyl-benzylsulfonyl)-pyrrolidin-2-yl]-1H-indole |
| 103 | 1-But-2-ynyl-2-[1-(2,5-dimethoxy-benzylsulfonyl)-pyrrolidin-2-yl]-3-phenyl-1H-indole |
| 104 | 1-[2-(1-But-2-ynyl-3-phenyl-1H-indol-2-yl)-pyrrolidin-1-yl]-3,3-dimethyl-butan-1-one |
| 105 | [2-(1-But-2-ynyl-3-phenyl-1H-indol-2-yl)-pyrrolidin-1-yl]-p-tolyl-methanone |
| 106 | 1-But-2-ynyl-2-[1-(5-chloro-thiophene-2-sulfonyl)-pyrrolidin-2-yl]-3-phenyl-1H-indole |
| 107 | 1-[2-(1-But-2-ynyl-3-phenyl-1H-indol-2-yl)-pyrrolidin-1-yl]-2-phenoxy-ethanone |
| 108 | [2-(1-But-2-ynyl-3-phenyl-1H-indol-2-yl)-pyrrolidin-1-yl]-4-methyl-3-nitro-phenyl)-methanone |
| 109 | [2-(1-But-2-ynyl-5-chloro-3-phenyl-1H-indol-2-yl)-pyrrolidin-1-yl]-(2,5-dimethyl-furan-3-yl)-methanone |
| 110 | Adamantan-1-yl-[2-(3-phenyl-1H-indol-2-yl)-pyrrolidin-1-yl]-methanone |
| 111 | [2-(1-But-2-ynyl-3-phenyl-1H-indol-2-yl)-pyrrolidin-1-yl]-(3,5-difluoro-phenyl)-methanone |
| 112 | [2-(1-But-2-ynyl-3-phenyl-1H-indol-2-yl)-pyrrolidin-1-yl]-cyclohexyl-methanone |
| 113 | 1-[2-(1-But-2-ynyl-3-phenyl-1H-indol-2-yl)-pyrrolidin-1-yl]-2-(3-methoxy-phenyl)-ethanone |
| 114 | (3-Fluoro-4-methyl-phenyl)-[2-(3-phenyl-1-prop-2-ynyl-1H-indol-2-yl)-pyrrolidin-1-yl]-methanone |
| 115 | 2-[1-(2-Chloro-benzylsulfonyl)-pyrrolidin-2-yl]-3-phenyl-1H-indole |
| 116 | 1-{7-[2-(1-But-2-ynyl-3-phenyl-1H-indol-2-yl)-pyrrolidines-1-sulfonyl]-3,4-dihydro-1H-isoquinolin-2-yl}-2,2,2-trifluoro-ethanone [sic] |
| 117 | 2-[1-(3-Chloro-4-fluorobenzylsulfonyl)-pyrrolidin-2-yl]-3-phenyl-1H-indole |
| 118 | 1-[2-(1-But-2-ynyl-3-phenyl-1H-indol-2-yl)-pyrrolidin-1-yl]-2-phenyl-butan-1-one |
| 119 | [2-(1-But-2-ynyl-3-phenyl-1H-indol-2-yl)-pyrrolidin-1-yl]-(1-phenyl-5-propyl-1H-[pyrazol-4-yl)-methanone |
| 120 | 1-[2-(1-But-2-ynyl-3-phenyl-1H-indol-2-yl)-pyrrolidin-1-yl]-2-(4-chloro-phenyl)-ethanone |
| 121 | [2-(1-But-2-ynyl-5-chloro-3-phenyl-1H-indol-2-yl)-pyrrolidin-1-yl]-(6-chloro-pyridin-3-yl)-methanone |
| 122 | [2-(1-But-2-ynyl-5-chloro-3-phenyl-1H-indol-2-yl)-pyrrolidin-1-yl]-(2-ethoxy-phenyl)-methanone |
| 123 | [2-(1-But-2-ynyl-3-phenyl-1H-indol-2-yl)-pyrrolidin-1-yl]-pyridin-2-yl-methanone |
| 124 | [2-(1-But-2-ynyl-5-chloro-3-phenyl-1H-indol-2-yl)-pyrrolidin-1-yl]-isoxazol-5-yl-methanone |

Biochemical Testing
NOS Assay
General

This assay allows the determination of the percentage inhibition of NO synthase by an active compound by means of measurement of the NOS activity under the action of the active compound. In this procedure, NO synthase is mixed together with radioactively labelled arginine and the active compound under suitable conditions. After discontinuation of the NO formation reaction at a given point in time, the amount of unreacted arginine is determined directly or indirectly. Comparison of this amount with the amount of arginine which remains in a sample from the mixture of NOS and arginine without the addition of active compound and under otherwise identical conditions gives the % inhibition of NO synthase by the active compound tested. This assay can be carried out as follows:

incubation of NO synthase with labelled arginine as the substrate in a reaction vessel, separation of the labelled arginine from the labelled citrulline possibly formed as the product of the enzymatic reaction at a point in time at which the concentration of citrulline increases, measurement of the amount of arginine separated off in the particular case.

The separation is carried out via a filter plate membrane.

This NOS assay is particularly suitable for a "high throughput screening" (HTS) on microtitre plates (MTP).

HTS NOS Assay: General Procedure

In this HTS NOS assay, radioactive arginine is used as the substrate. The assay volume can be chosen in the range between 25 μl and 250 μl, depending on the nature of the microtitre plate (MTP). Cofactors and coenzymes are added, depending on the enzyme source used. The incubation of the batches in this microtitre plate (assay MTP) according to step (a) is carried out at room temperature and is between 5 and 60 minutes, depending on the enzyme activity (units) used. At the end of the incubation (step (a)), the plate is placed in a cell harvester equipped with an MTP which has a cation exchange membrane as the filter base (filter MTP). All the batches of the assay MTP are transferred into this filter MTP and filtered with suction over a cation exchanger filter plate, a paper filter loaded with phosphate groups. The filter MTP is then washed with buffer or water. The arginine substrate which remains is bonded to the cation exchanger with the aid of this procedure, while the radioactive citrulline formed enzymatically is washed out quantitatively. After drying of the filter MTP and addition of scintillation liquid, the arginine bonded can be counted on a scintillation counter. A non-inhibited NOS reaction is reflected in a low radioactivity. An inhibited enzyme reaction means that the radioactive arginine has not been reacted, i.e. there is a high radioactivity on the filter.

Materials Used

Arginine, L-[2,3,4-$^3$H]-monohydrochloride; order no. NET-1123, NEN $CaCl_2$, anhydrous; order no. 2388.1000; Merck KGaA 1,4-dithiothreitol (DTT), order no. 708984; ROCHE $Na_2$EDTA-dihydrate; order no. 03680; FLUKA HEPES, order no. H-3375; SIGMA NADPH, tetrasodium salt; order no. 1585363; ROCHE TRIS; ORDER no. 93349; FLUKA Enzyme preparation buffer: 50 mM Tris-HCl with 1 mM EDTA: The pH of the buffer was adjusted to 7.4 at 4° C.

Incubation buffer (medium): 50 mM HEPES with 1 mM EDTA; 1.25 mM $CaCl_2$ and 1 mM dithiothreitol.

The pH of the buffer was adjusted to 7.4 at 25° C.

Washing medium: $H_2O$

Enzyme Preparation

Rat cerebelli were used as the starting tissue. The animals were narcotized and sacrificed, the brain tissue, the cerebellum, was removed, 1 ml of enzyme preparation buffer was added (4° C.) per rat cerebellum and the tissue was broken down with a Polytron homogeniser for 1 min at 6,000 rpm. Centrifugation at 4° C. for 15 min at 20,000 g and subsequent decanting of the supernatant and freezing in portions at −80° C. (precipitate discarded) then took place.

Test Results

Compounds according to the invention were tested for nNOS inhibition in the NOS assay described above. The results are reproduced in table 2.

TABLE 2

| Example no. | Compound | NNOS inhibition (10 μm) [%] |
|---|---|---|
| 9 | {2-[5-Chloro-1-(2-diethylamino-ethyl)-3-phenyl-1H-indol-2-yl]-pyrrolidin-1-yl)-furan-2-yl-methanone | 45 |
| 12 | 4-{2-[5-Chloro-1-(2-diethylamino-ethyl)-3-phenyl-1H-indol-2-yl]-pyrrolidin-1-yl}-4-oxo-butyric acid ethyl ester | 34 |
| 13 | {2-[5-Chloro-1-(2-diethylamino-ethyl)-3-phenyl-1H-indol-2-yl]-pyrrolidin-1-yl}-(4-fluoro-phenyl)-methanone | 47 |
| 15 | {2-[5-Chloro-1-(2-diethylamino-ethyl)-3-phenyl-1H-indol-2-yl]-pyrrolidin-1-yl)-cyclobutyl-methanone | 38 |
| 17 | {2-[5-Chloro-1-(2-diethylamino-ethyl)-3-phenyl-1H-indol-2-yl]-pyrrolidin-1-yl}-(6-chloro-pyridin-3-yl)-methanone | 36 |
| 20 | 1-{2-[5-Chloro-1-(2-diethylamino-ethyl)-3-phenyl-1H-indol-2-yl]-pyrrolidin-1-yl}-hexan-1-one | 35 |
| 26 | {2-[5-Chloro-1-(2-diethylamino-ethyl)-3-phenyl-1H-indol-2-yl]-pyrrolidin-1-yl}-(3,5-dimethoxy-phenyl)-methanone | 51 |
| 28 | {2-[5-Chloro-1-(2-diethylamino-ethyl)-3-phenyl-1H-indol-2-yl]-pyrrolidin-1-yl}-(4-ethoxy-phenyl)-methanone | 41 |
| 35 | 1-[2-(5-Chloro-1-methyl-3-phenyl-1H-indol-2-yl)-pyrrolidin-1-yl]-2-(2-methoxy-ethoxy)-ethanone | 41 |
| 48 | [2-(5-Chloro-1-methyl-3-phenyl-1H-indol-2-yl)-pyrrolidin-1-yl]-cyclopropyl-methanone | 35 |
| 73 | 1-[2-(1-But-2-ynyl-5-chloro-3-phenyl-1H-indol-2-yl)-pyrrolidin-1-yl]-2-methoxy-ethanone | 54 |

The known NOS inhibitor 7-nitroindazole was tested as a comparison example in this NOS assay with an inhibition (10 μM) of 50%.

Pharmaceutical Formulation of a Medicament According to the Invention 1 g 1-[2-(1-but-2-ynyl-5-chloro-3-phenyl-1H-indol-2-yl)-pyrrolidin-1-yl]-2-methoxy-ethanone is dissolved in 1 l of water for injection at room temperature and the solution is then adjusted to isotonic conditions by addition of sodium chloride.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A substituted 2-pyrrolidin-2-yl-1H-indole compound corresponding to formula (I)

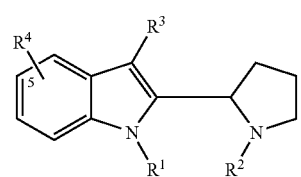

I wherein
R¹ denotes H, alkyl, cycloalkyl, alkyl-cycloalkyl, alkyl-aryl or alkyl-heterocyclyl;
R² denotes H, alkyl, cycloalkyl, alkyl-cycloalkyl, alkyl-aryl, alkyl-heterocyclyl, C(=O)—R²⁰ or SO₂—R²¹;
R³ denotes alkyl, aryl or heterocyclyl;
R⁴ denotes H, F, Cl, Br, I, —CN, OR⁴⁰, alkyl, cycloalkyl or NO₂;
R²⁰ denotes alkyl, cycloalkyl, alkyl-cycloalkyl, aryl, alkyl-aryl, heterocyclyl, alkyl-heterocyclyl, OR²⁰⁰ or NHR²⁰¹;
R²¹ denotes alkyl, aryl, alkyl-aryl, heterocyclyl or alkyl-heterocyclyl;
R⁴⁰ denotes H, alkyl, cycloalkyl, alkyl-cycloalkyl, aryl or alkyl-aryl;
R²⁰⁰ denotes alkyl, cycloalkyl, alkyl-cycloalkyl, aryl, alkyl-aryl, heterocyclyl or alkyl-heterocyclyl; and
R²⁰¹ denotes alkyl, aryl, alkyl-aryl, heterocyclyl or alkyl-heterocyclyl;
or a salt thereof with a physiologically tolerated acid, provided that 2-(3-phenyl-1H-indol-2-yl)-1-(trifluoroacetyl)-pyrrolidine; α-methyl-2-(1-methyl-2-pyrrolidinyl)-indole-3-acetic acid methyl ester; 3-(1-cyanoethyl)-2-(1-methyl-2-pyrrolidinyl)-indole; and 2-(1-methyl-2-pyrrolidinyl)-3-vinylindole are excluded.

2. The compound of claim 1, wherein said compound is present in the form of a free base.

3. The compound of claim 1, wherein said compound is present in the form of a pure enantiomer or pure diastereoisomer.

4. The compound of claim 1, wherein said compound is present in the form of a mixture of stereoisomers.

5. The compound of claim 1, wherein said compound is present in the form of a racemic mixture.

6. The compound of claim 1, wherein said compound is present in the form of a solvate.

7. The compound of claim 1, wherein said compound is present in the form of a hydrate.

8. A substituted 2-pyrrolidin-2-yl-1H-indole compound according to claim 1, wherein
R¹ denotes H, alkyl, cycloalkyl or alkyl-cycloalkyl;
R² denotes C(=O)—R²⁰ or SO₂—R²¹;
R³ denotes aryl;
R⁴ denotes H, F, Cl, Br, I, —CN, OR⁴⁰, alkyl, cycloalkyl or NO₂, in each case in the 5-position of the indole ring;
R²⁰ denotes alkyl, cycloalkyl, alkyl-cycloalkyl, aryl, alkyl-aryl, heterocyclyl or alkyl-heterocyclyl;
R²¹ denotes alkyl, aryl, alkyl-aryl, heterocyclyl or alkyl-heterocyclyl; and
R⁴⁰ denotes H, alkyl, cycloalkyl, alkyl-cycloalkyl, aryl or alkyl-aryl.

9. A substituted 2-pyrrolidin-2-yl-1H-indole compound according to claim 1, wherein
R¹ denotes H or alkyl;
R² denotes C(=O)—R²⁰ or SO₂—R²¹;
R³ denotes phenyl;
R⁴ denotes H, F, Cl, Br or I, in each case in the 5-position of the indole ring;
R²⁰ denotes $C_{1-8}$-alkanyl, $C_{2-8}$-alkenyl, $C_{1-4}$-alkanyl-CO₂—$C_{1-4}$-alkyl, $C_{1-4}$-alkanyl-O—R²⁰², $C_{1-4}$-alkanyl-NR²⁰³R²⁰⁴, $C_{3-8}$-cycloalkyl, 1-adamantyl, 2-adamantyl, —($C_{1-3}$-alkyl)-$C_{3-8}$-cycloalkyl, aryl¹, aryl², $C_{1-4}$-alkanyl-aryl³, $C_{2-4}$-alkenyl-aryl⁴; or unsubstituted or substituted furanyl, pyrazolyl, isoxazolyl or pyridinyl; or 4,7,7-trimethyloxabicyclo [2.2.1]heptan-3-one, —CH₂-imidazolidine-2,4-dione;

R²¹ denotes aryl⁵, unsubstituted or substituted thienyl or represents

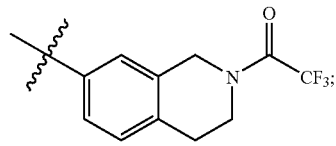

R²⁰² denotes H, $C_{1-4}$-alkanyl, $C_{1-4}$-alkanyl-OH, $C_{1-4}$-alkanoyl-O—$C_{1-4}$-alkanyl or aryl;
R²⁰³ and R²⁰⁴ independently of one another denote $C_{1-6}$-alkyl or, with the N atom, form a 5-, 6- or 7-membered saturated heterocyclyl;

aryl¹ represents

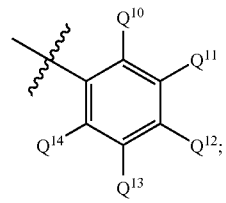

aryl² represents

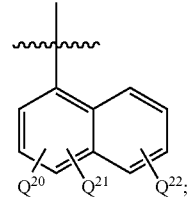

aryl³ represents

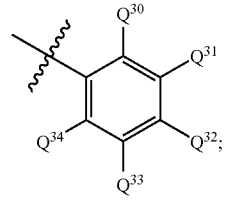

aryl⁴ represents

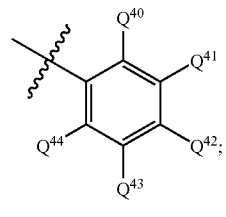

aryl⁵ represents

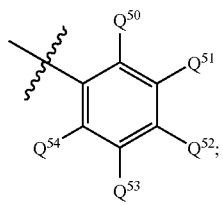

and

Q¹⁰, Q¹¹, Q¹², Q¹³, Q¹⁴, Q²⁰, Q²¹, Q²², Q³⁰, Q³¹, Q³², Q³³, Q³⁴, Q⁴⁰, Q⁴¹, Q⁴², Q⁴³, Q⁴⁴, Q⁵⁰, Q⁵¹, Q⁵², Q⁵³ and Q⁵⁴ independently of one another denote H, F, Cl, Br, I, —CN, —NO₂, $C_{1-4}$-alkyl, OH, O—$C_{1-4}$-alkyl, SH or S—$C_{1-4}$-alkyl.

10. A substituted 2-pyrrolidin-2-yl-1H-indole compound according to claim 9, wherein R¹ denotes H, methyl, but-2-yne or diethylaminoethyl;
R² denotes C(=O)—R²⁰ or SO₂—R²¹;
R³ denotes phenyl;
R⁴ denotes 5-H or 5-Cl;
R²⁰ denotes methyl, ethyl, n-propyl, n-butyl, 1-methylpropyl, 2-methylpropyl, tert-butyl, n-pentyl, 1-methylbutyl, 2,2-dimethylpropyl, 1-propylbutyl, 1-ethylpentyl, prop-1-enyl, prop-2-enyl, but-1-enyl, but-2-enyl, but-3-enyl, —(CH₂)₂—CO₂-methyl, —(CH₂)₂—CO₂-ethyl, —CH₂—O—CH₃, —O—(CH₂)₂—O—CH₃, —CH₂—O-phenyl, —CH₂—O-(4-chlorophenyl), —CH(CH₃)—O-phenyl, —(CH₂)₃—O-phenyl), dimethylaminomethyl, cyclopropyl, cyclobutyl, cyclopentyl, cyclohexyl, 1-adamantyl, —CH₂-cyclopropyl, —CH₂-cyclopentyl, aryl¹, 1-naphthyl, CH₂-aryl³, —CH(C₂H₅)-aryl³, —CH=CH-aryl⁴, furan-2-yl, furan-3-yl, 5-tert-butyl-2-methyl-furan-3-yl, 2,5-dimethyl-furan-3-yl, pyrazol-4-yl, pyrazol-5-yl, 1-tert-butyl-3-methyl-pyrazol-5-yl, 1-phenyl-3-propyl-pyrazol-4-yl, isoxazol-3-yl, isoxazol-4-yl, isoxazol-5-yl, 5-methyl-4-(2-chlorophenyl)-isoxazol-3-yl, 5-methyl-3-(2-chloro-6-fluorophenyl)-isoxazol-4-yl, pyridin-2-yl, pyridin-3-yl, pyridin-4-yl, 2-chloropyridin-3-yl, 6-chloropyridin-3-yl, 2-(CH₃—S—)-pyridin-3-yl, 2-methyl-6-trifluoromethyl-pyridin-3-yl, 4,7,7-trimethyloxabicyclo[2.2.1]heptan-3-one or —CH₂-imidazolidine-2,4-dione;
R²¹ denotes aryl⁵, thien-2-yl, thien-3-yl or 5-chloro-thien-2-yl or represents

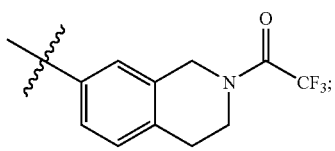

aryl¹ represents

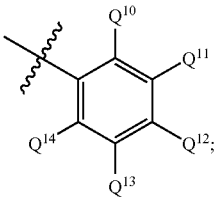

aryl³ represents

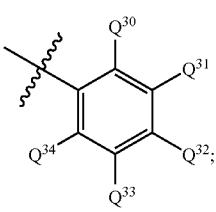

aryl⁴ represents

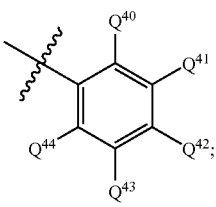

aryl⁵ represents

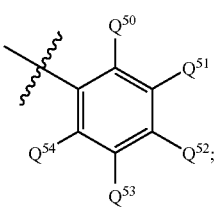

Q¹⁰, Q¹¹, Q¹², Q¹³ and Q¹⁴ independently of one another denote H, F, Cl, Br, —NO₂, methyl, trifluoromethyl, ethyl, n-propyl, 1-methylethyl, O—CH₃, O—CF₃, —O—C₂H₅, S—CH₃ or S—CF₃;
Q³⁰, Q³¹, Q³², Q³³ and Q³⁴ independently of one another denote H, Cl or O—CH₃;
Q⁴⁰, Q⁴¹, Q⁴², Q⁴³ and Q⁴⁴ independently of one another denote H, Cl, CH₃ or CF₃; and
Q⁵⁰, Q⁵¹, Q⁵², Q⁵³ and Q⁵⁴ independently of one another denote H, F, Cl, Br, methyl, ethyl, n-propyl, 1-methylethyl, O—CH₃, O—CF₃, O—CH₂CH₃, O—CH₂CH₂CH₃, or O—CH₂CH₂CH₂CH₃.

11. A substituted 2-pyrrolidin-2-yl-1H-indole compound according to claim 10, wherein R¹ denotes H, methyl, but-2-yne or diethylaminoethyl;
R² denotes C(=O)—R²⁰ or SO₂—R²¹;
R³ denotes phenyl;
R⁴ denotes 5-H or 5-Cl;

R²⁰ denotes n-propyl, n-butyl, n-pentyl, 1-methylbutyl, 2,2-dimethylpropyl, 1-propylbutyl, 1-ethylpentyl, but-3-enyl, —(CH₂)₂—CO₂-methyl, —(CH₂)₂—CO₂-ethyl, —CH₂—O—CH₃, —CH₂—O—(CH₂)₂—O—CH₃, —CH₂—O-phenyl, —CH₂—O—(4-chlorophenyl), —CH(CH₃)—O-phenyl, —(CH₂)₃—O-phenyl, dimethylaminomethyl, cyclopropyl, cyclobutyl, cyclohexyl, 1-adamantyl, —CH₂-cyclopentyl, 4-fluorophenyl, 4-chlorophenyl, 2-bromophenyl, 3-bromophenyl, 2,3-difluorophenyl, 3-fluoro-4-trifluoromethylphenyl, 3-fluoro-6-trifluoromethylphenyl, 3-fluoro-4-methylphenyl, 3,5-difluorophenyl, 2-chloro-4-nitrophenyl, 2-chloro-5-trifluoromethylphenyl, 4-bromo-3-methylphenyl, 2,3-difluoro-4-methylphenyl, 2,6-difluoro-3-methylphenyl, 2,3,4,5,6-pentafluorophenyl, 4-nitrophenyl, 4-methyl-3-nitrophenyl, 3-methylphenyl, 4-methylphenyl, 2,3-dimethylphenyl, 3-trifluoromethylphenyl, 2,5-trifluoromethylphenyl, 3,5-trifluoromethylphenyl, 4-ethylphenyl, 4-n-propylphenyl, 3-methoxyphenyl, 3,5-dimethoxyphenyl, 3-trifluoromethoxyphenyl, 4-trifluoromethoxyphenyl, 2-ethoxyphenyl, 4-ethoxyphenyl, 4-S—CF₃-phenyl, benzyl, 4-chlorobenzyl, 3-methoxybenzyl, 2,5-dimethoxybenzyl, —CH(C₂H₅)-phenyl, —CH=CH-(2-chlorophenyl), —CH=CH-(3-trifluoromethylphenyl), furan-2-yl, 5-tert-butyl-2-methyl-furan-3-yl, 2,5-dimethyl-furan-3-yl, 1-tert-butyl-3-methyl-pyrazol-5-yl, 1-phenyl-3-propyl-pyrazol-4-yl, isoxazol-5-yl, 5-methyl-4-(2-chlorophenyl)-isoxazol-3-yl, 5-methyl-3-(2-chloro-6-fluorophenyl)-isoxazol-4-yl, pyridin-2-yl, 2-chloropyridin-3-yl, 6-chloropyridin-3-yl, 2-(CH₃—S—)-pyridin-3-yl, 2-methyl-6-trifluoromethyl-pyridin-3-yl, 4,7,7-trimethyloxabicyclo [2.2.1] heptan-3-one or —CH₂-imidazolidine-2,4-dione; and R²¹ denotes 3-chloro-4-fluorophenyl, 2-chlorophenyl, 4-chlorophenyl, 3-chloro-2-methylphenyl, 3-bromophenyl, 2,3,5,6-tetramethylphenyl, 4-n-butylphenyl, 4-methoxyphenyl, 2,5-dimethoxyphenyl, 4-trifluoromethoxyphenyl, 4-(n-butoxy)-phenyl, thien-2-yl, 5-chlorothien-2-yl or represents

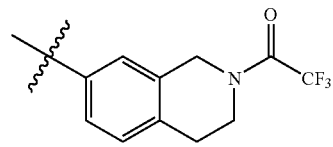

12. A substituted 2-pyrrolidin-2-yl-1H-indole compound according to claim 1, wherein said compound is selected from the group consisting of:
{2-[5-chloro-1-(2-diethylamino-ethyl)-3-phenyl-1H-indol-2-yl]-pyrrolidin-1-yl}-furan-2-yl-methanone;
4-{2-[5-chloro-1-(2-diethylamino-ethyl)-3-phenyl-1H-indol-2-yl]-pyrrolidin-1-yl}-4-oxo-butyric acid ethyl ester;
{2-[5-chloro-1-(2-diethylamino-ethyl)-3-phenyl-1H-indol-2-yl]-pyrrolidin-1-yl}-(4-fluoro-phenyl)-methanone;
{2-[5-chloro-1-(2-diethylamino-ethyl)-3-phenyl-1H-indol-2-yl]-pyrrolidin-1-yl}-cyclobutyl-methanone;
{2-[5-chloro-1-(2-diethylamino-ethyl)-3-phenyl-1H-indol-2-yl]-pyrrolidin-1-yl}-(6-chloro-pyridin-3-yl)-methanone;
1-{2-[5-chloro-1-(2-diethylamino-ethyl)-3-phenyl-1H-indol-2-yl]-pyrrolidin-1-yl}-hexan-1-one;
{2-[5-chloro-1-(2-diethylamino-ethyl)-3-phenyl-1H-indol-2-yl]-pyrrolidin-1-yl}-(3,5-dimethoxy-phenyl)-methanone;
{2-[5-chloro-1-(2-diethylamino-ethyl)-3-phenyl-1H-indol-2-yl]-pyrrolidin-1-yl}-(4-ethoxy-phenyl)-methanone;
1-[2-(5-chloro-1-methyl-3-phenyl-1H-indol-2-yl)-pyrrolidin-1-yl]-2-(2-methoxy-ethoxy)-ethanone;
[2-(5-chloro-1-methyl-3-phenyl-1H-indol-2-yl)-pyrrolidin-1-yl]-cyclopropyl-methanone; and
1-[2-(1-but-2-ynyl-5-chloro-3-phenyl-1H-indol-2-yl)-pyrrolidin-1-yl]-2-methoxy-ethanone.

13. A pharmaceutical formulation comprising at least one compound corresponding to formula (I)

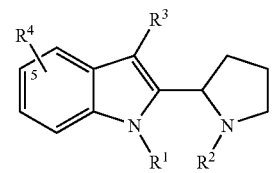

wherein
R¹ denotes H, alkyl, cycloalkyl, alkyl-cycloalkyl, alkyl-aryl or alkyl-heterocyclyl;
R² denotes H, alkyl, cycloalkyl, alkyl-cycloalkyl, alkyl-aryl, alkyl-heterocyclyl, C(=O)—R²⁰ or SO₂—R²¹;
R³ denotes alkyl, aryl or heterocyclyl;
R⁴ denotes H, F, Cl, Br, I, —CN, OR⁴⁰, alkyl, cycloalkyl or NO₂;
R²⁰ denotes alkyl, cycloalkyl, alkyl-cycloalkyl, aryl, alkyl-aryl, heterocyclyl, alkyl-heterocyclyl, OR²⁰⁰ or NHR²⁰¹;
R²¹ denotes alkyl, aryl, alkyl-aryl, heterocyclyl or alkyl-heterocyclyl;
R⁴⁰ denotes H, alkyl, cycloalkyl, alkyl-cycloalkyl, aryl or alkyl-aryl;
R²⁰⁰ denotes alkyl, cycloalkyl, alkyl-cycloalkyl, aryl, alkyl-aryl, heterocyclyl or alkyl-heterocyclyl; and
R²⁰¹ denotes alkyl, aryl, alkyl-aryl, heterocyclyl or alkyl-heterocyclyl,
or a salt thereof with a physiologically tolerated acid, and a pharmaceutically acceptable excipient.

14. The pharmaceutical formulation of claim 13, wherein said compound is present in the form of a free base.

15. The pharmaceutical formulation of claim 13, wherein said compound is present in the form of a pure enantiomer or pure diastereoisomer.

16. The pharmaceutical formulation of claim 13, wherein said compound is present in the form of a mixture of stereoisomers.

17. The pharmaceutical formulation of claim 13, wherein said compound is present in the form of a racemic mixture.

18. The pharmaceutical formulation of claim 13, wherein said compound is present in the form of a solvate.

19. The pharmaceutical formulation of claim 13, wherein said compound is present in the form of a hydrate.

* * * * *